United States Patent [19]

Lindel et al.

[11] Patent Number: 5,028,617

[45] Date of Patent: Jul. 2, 1991

[54] HETEROARYLETHANOL-PYRIDYLALK-YLAMINES FOR CONTROLLING ANIMAL GROWTH

[75] Inventors: Hans Lindel, Leverkusen; Werner Hallenbach, Monheim; Friedrich Berschauer, Wuppertal; Heinrich A. Greife, Langenfeld; Gernot Klotz, Leichlingen, all of Fed. Rep. of Germany

[73] Assignee: Bayer Aktiengesellschaft, Leverkusen, Fed. Rep. of Germany

[21] Appl. No.: 467,593

[22] Filed: Jan. 19, 1990

[30] Foreign Application Priority Data

Jan. 26, 1989 [DE] Fed. Rep. of Germany ....... 3902286
Jun. 9, 1989 [DE] Fed. Rep. of Germany ....... 3918834

[51] Int. Cl.$^5$ .................... A61K 31/44; C07D 401/12
[52] U.S. Cl. ................................ 514/332; 514/335; 546/261; 546/264
[58] Field of Search ............... 546/261, 264; 514/335, 514/332

[56] References Cited

FOREIGN PATENT DOCUMENTS 0026298 4/1981 European Pat. Off. .
0170538 2/1986 European Pat. Off. .
0256420 8/1988 European Pat. Off. .

*Primary Examiner*—Mary C. Lee
*Assistant Examiner*—Jacqueline Haley
*Attorney, Agent, or Firm*—Sprung Horn Kramer & Woods

[57] ABSTRACT

A compound for promoting livestock production and for controlling obesity in humans and animals, of the formula

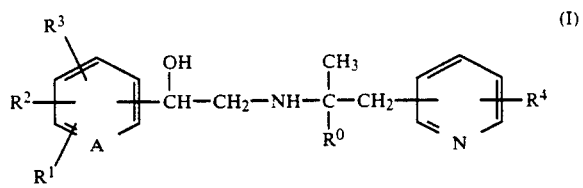

in which
A represents =CH— or =N—,
$R^0$ represents hydrogen or methyl,
$R^1$ and $R^3$ each independently represents hydrogen, hydroxyl, halogen, cyano, alkyl, halogenoalkyl, hydroxyalkyl, alkoxycarbonyl, aminocarbonyl, mono- and dialkylaminocarbonyl, alkoxy, halogenoalkoxy, halogenoalkylthio, $NHSO_2$-alkyl,
$R^2$ represents hydrogen, hydroxyl, alkoxy or the radical —$NR^5R^6$,
$R^4$ represents hydrogen, $C_1$–$C_{10}$-alkyl which is optionally substituted by hydroxyl, halogen, alkoxy, acyloxy or the radical —$NH^7R^8$, or represents the radical $COR^9$ or the radical —O—Z—$R^{10}$,
Z represents $C_1$–$C_{10}$-alkylene, -alkenylene or alkynylene,
$R^5$ represents hydrogen or alkyl,
$R^6$ represents hydrogen, alkyl, halogenoalkyl or acyl, or $R^5$ and $R^6$ together with the adjoining N atom form a saturated or unsaturated heterocyclic 4-, 5- or 6-membered ring,
$R^7$ and $R^8$ each independently represents hydrogen, optionally substituted alkyl, optionally substituted aryl,
$R^9$ represents hydroxyl, alkoxy or the radical —$NR^7R^8$,
$R^{10}$ represents hydroxyl, alkoxy, acyloxy, optionally substituted aryloxy or aralkyloxy, with the substituent $R^4$ and the alkylamino group in the pyridyl ring of the formula I being in the p position with respect to one another, or a physiologically tolerated salt thereof, or, if A represents nitrogen, optionally the N-oxide thereof.

6 Claims, No Drawings

HETEROARYLETHANOL-PYRIDYLALKYLAMINES FOR CONTROLLING ANIMAL GROWTH

The present invention relates to new aryl- and heteroarylethanol-pyridylalkylamines, process for the preparation thereof and the use thereof as production promoters in livestock and as agents for treating obesity in humans and animals.

Aryl- and heteroarylethanolamines have already been disclosed. They are suitable as production promoters for livestock. However, their action is not satisfactory in every case. (European Published Specifications 26,298; 254,856; 170,538; 256,420)

The following have now been found:

1. New aryl- and heteroarylethanol-pyridylamines of the formula I

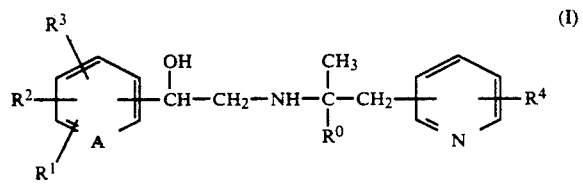

in which

A represents =CH— or =N—, $R^0$ represents hydrogen or methyl, $R^1$ represents hydrogen, hydroxyl, halogen, cyano, alkyl, halogenoalkyl, hydroxyalkyl, alkoxycarbonyl, aminocarbonyl, mono- and dialkylaminocarbonyl, alkoxy, halogenoalkoxy, halogenoalkylthio or $NHSO_2$-alkyl, $R^2$ represents hydrogen, hydroxyl, alkoxy or the radical —$NR^5R^6$, $R^3$ represents the radicals specified for $R^1$, $R^4$ represents hydrogen, $C_1$-$C_{10}$-alkyl which is optionally substituted by hydroxyl, halogen, alkoxy, acyloxy or the radical —$NR^7R^8$, and represents the radical $COR^9$ or the radical —O—Z—$R^{10}$, Z represents $C_1$-$C_{10}$-alkylene, -alkenylene or alkynylene, $R^5$ represents hydrogen or alkyl, $R^6$ represents hydrogen, alkyl, halogenoalkyl or acyl, it being possible for $R^5$ and $R^6$ to form, together with the adjoining N atom, a saturated or unsaturated heterocyclic 4-, 5- or 6-membered ring, $R^7$ represents hydrogen, optionally substituted alkyl, optionally substituted aryl, $R^8$ represents the radicals specified for $R^7$, $R^9$ represents hydroxyl, alkoxy or the radical —$NR^7R^8$, $R^{10}$ represents hydroxyl, alkoxy, acyloxy, optionally substituted aryloxy or aralkyloxy, with the substituent $R^4$ and the alkylamino group in the pryridyl ring of the formula I being in the p position with respect to one another as well as the physiologically tolerated salts thereof and, if A represents nitrogen, the N-oxides thereof.

2. Process for the preparation of the compounds of the formula I

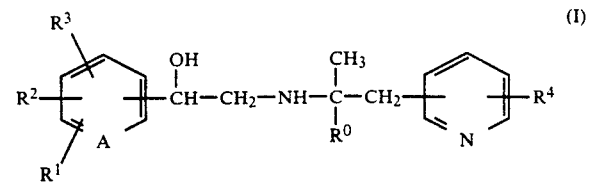

in which

A represents =CH— or =N—, $R^0$ represents hydrogen or methyl, $R^1$ represents hydrogen, alkyl, halogen, halogenoalky, cyano, hydroxyl, hydroxyalkyl, alkoxycarbonyl, aminocarbonyl, mono- and dialkylaminocarbonyl, alkoxy, halogenoalkoxy, halogenoalkylthio or $NHSO_2$.alkyl, $R^2$ represents hydrogen, hydroxyl, alkoxy or the radical —$NR^5R^6$, $R^3$ represents the radicals specified for $R^1$, $R^4$ represents hydrogen, $C_1$-$C_{10}$-alkyl which is optionally substituted by hydroxyl, halogen, alkoxy, acyloxy or the radical —$NR^7R^8$, and represents the radical $COR^9$ or the radical —O—Z—$R^{10}$, Z represents $C_1$-$C_{10}$-alkylene, -alkenylene or alkynylene, $R^5$ represents hydrogen or alkyl, $R^6$ represents hydrogen, alkyl, halogenoalkyl or acyl, it being possible for $R^5$ and $R^6$ to form, together with the adjoining N atom, a saturated or unsaturated heterocyclic 4-, 5- or 6-membered ring, $R^7$ represents hydrogen, optionally substituted alkyl, optionally substituted aryl, $R^8$ represents the radicals specified for $R^7$, $R^9$ represents hydroxyl, alkoxy or the radical —$NR^7R^8$, $R^{10}$ represents hydroxyl, alkoxy, acyloxy, optionally substituted aryloxy or aralkyloxy, with the substituent $R^4$ and the alkylamino group in the pyridyl ring of the formula I being in the p position with respect to one another, a) by reacting halogenomethyl ketones of the formula II

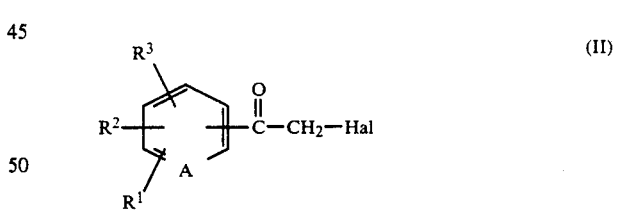

in which $R^1$ to $R^3$ and A have the meanings specified above, and Hal represents halogen,
with amines of the formula (III)

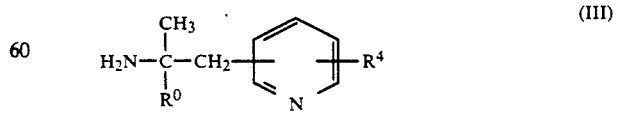

in which $R^0$ and $R^4$ have the meanings specified above and $R^4$ is in the p position with respect to the alkylamine residue, and subsequently reducing the carbonyl group, or b) by reacting epoxides of the formula IV

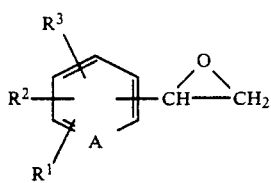
(IV)

in which
R¹ to R³ and A have the meanings specified above,
with amines of the formula III

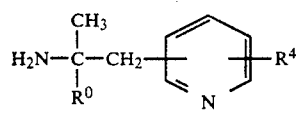
(III)

in which
$R^0$ and $R^4$ have the meanings specified above and $R^4$ is in the p position with respect to the alkylamine residue,
or c) by reacting β-halogenoethyl compounds of the formula V

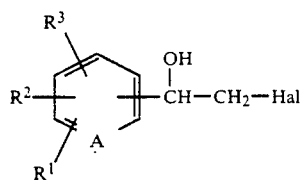
(V)

in which
R¹ to R³ and A have the meanings specified above, and Hal represents halogen,
with amines of the formula III

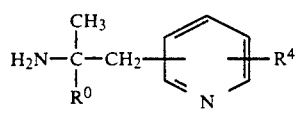
(III)

in which
$R^0$ and $R^4$ have the meanings specified above and $R^4$ is in the p position with respect to the alkylamine residue,
or d) in the case where $R^0$ represents hydrogen, by reacting compounds of the formula VI

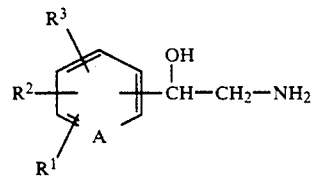
(VI)

in which
R¹ to R³ and A have the meanings specified above,
with ketones of the formula VII

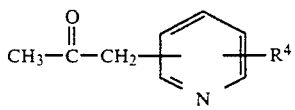
(VII)

in which
$R^4$ has the meaning specified above and is in the p position with respect to the acetonyl radical,
under reducing conditions, or e) by reacting compounds of the formula VIII

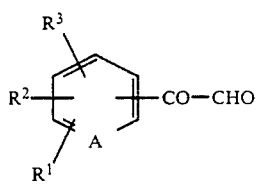
(VIII)

in which
R¹ to R³ and A have the meanings specified above,
with amines of the formula III

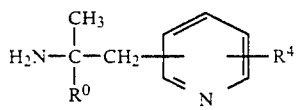
(III)

in which
$R^0$ and $R^4$ have the meanings specified above and $R^4$ is in the p position with respect to the alkylamine residue,
under reducing conditions, or f) by reducing compounds of the formula IX

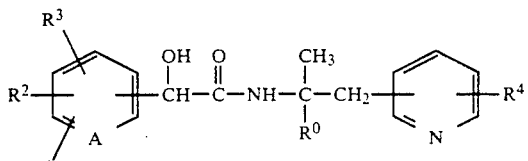
(IX)

in which
A and $R^0$ to $R^4$ have the meanings specified above, and $R^4$ and the other substituent in the pyridine ring of the formula IX are in the p position with respect to one another.

3. New compounds of the formula III

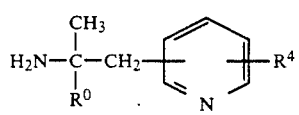
(III)

in which
$R^0$ and $R^4$ have the meanings specified for the compounds of the formula I but $R^4$ does not represent hydrogen, and the substituents on the pyridine ring are in the p position with respect to one another.

4. Process for the preparation of the compounds of the formula III according to 3, characterized in that
a) in the case where $R^0$ represents hydrogen, compounds of the formula VII

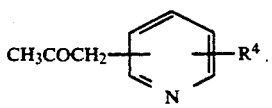
(VII)

in which

R$^4$ has the meanings the compounds of the formula I, and the substituents on the pyridine ring of the formula (VII) are in the p position with respect to one another a) are reduced in the presence of ammonia or b) are converted into the oxime thereof, the oxime ether or ester thereof, and the latter are subsequently reduced, or in that b) in the case where R$^0$ represents methyl, compounds of the formula (XXII)

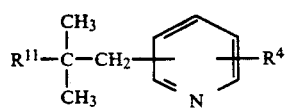
(XXII)

in which

R$^4$ has the meaning specified above, and

R$^{11}$ represents the radicals —NH—COCH$_3$ or —N-H—CHO, are reacted with bases.

5. New compounds of the formula IX

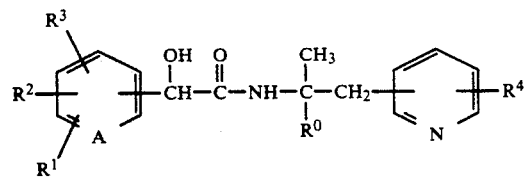
(IX)

in which

A and R$^0$ to R$^4$ have the meanings specified for the compounds of the formula I, with R$^4$ and the alkylamine side-chain in the pyridine ring of the formula (IX) being in the p position with respect to one another.

6. Process for the preparation of the compounds of the formula IX according to 5, characterized in that compounds of the formula X

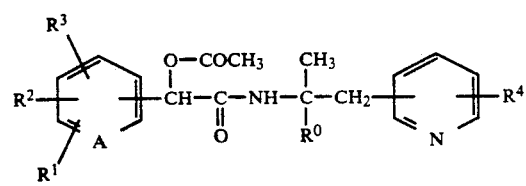
(X)

in which

A and R$^0$ to R$^4$ have the meanings specified above, and R$^4$ and the alkylamine side-chain in the pyridine ring are in the p position with respect to one another, are subjected to hydrolisis.

7. New compounds of the formula X

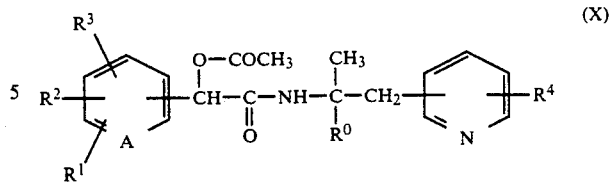
(X)

in which

R$^0$ to R$^4$ and A have the meanings specified above, and R$^4$ and the alkylamine side-chain in the pyridine ring are in the p position with respect to one another.

8. Process for the preparation of the compounds of the formula X according to 7, characterized in that aldehydes of the formula XI

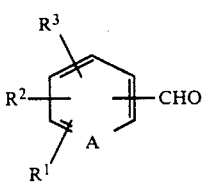
(XI)

in which

R$^1$ to R$^3$ and A have the meanings specified above, are reacted with isonitriles of the formula XII

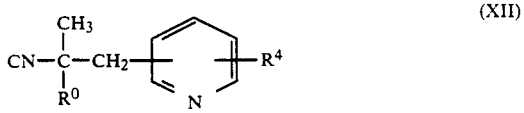
(XII)

in which

R$^0$ and R$^4$ has the meanings specified above, and the substituents on the pyridine ring of the formula (XII) are in the p position with respect to one another, in the presence of acetic acid.

9. New compounds of the formula XII

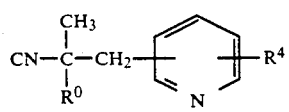
(XII)

in which

R$^0$ and R$^4$ have the meanings specified above, and the substituents on the pyridine ring of the formula (XII) are in the p position with respect to one another.

10. Process for the preparation of the compounds of the formula XII according to 9, characterized in that amines of the formula III

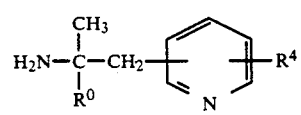
(III)

in which

R$^0$ and R$^4$ have the meanings specified above, and the substituents on the pyridine ring of the formula (III) are in the p position with respect to one another, are, in a manner known per se, initially converted into the formyl compound and the latter is then reacted with phosgene or phosphorus oxychloride.

11. New compounds of the formula XIII

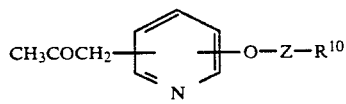
(XIII)

in which

R¹⁰ and Z have the meanings specified above at (1) and the substituents on the pyridine ring of the formula (XIII) are in the p position with respect to one another.

12. Process for the preparation of the compounds of the formula XIII according to 11, characterized in that a) in the case where the acetonyl group is in the 2 position and the radical —O—Z—R¹⁰ is in the 5 position, compounds of the formula XIV

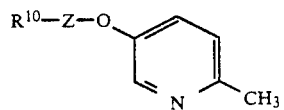
(XIV)

in which

R¹⁰ and Z have specified above, are lithiated and subsequently reacted with N,N-dimethylacetamide, b) in the case where the acetonyl group is in the 3 position and the radical —O—Z—R¹⁰ is in the 6 position, compounds of the formula XV

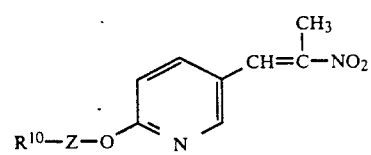
(XV)

in which

R¹⁰ and Z have meanings specified above, are reduced and hydrolysed.

13. New compounds of the formula XVI

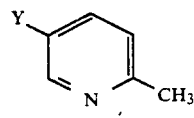
(XVI)

in which

Y represents —O13 X—R¹⁰, excepting 2-methoxyethoxy or 2-ethoxyethoxy.

14. Process for the preparation of the compounds of the formula XVI according to 13, characterized in that 2-methyl-5-hydroxypyridine is alkylated with a compound of the formula XVII

R¹⁰—Z—X  (XVII)

in which

R¹⁰ and Z have the meanings specified above, and X represents halogen, mesylate or tosylate.

15. New compounds of the formula XV

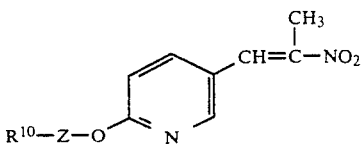
(XV)

in which

R¹⁰ and Z have the meanings specified above, where R¹⁰—Z—does not represent methyl.

16. Process for the preparation of the compounds of the formula XV according to 15, characterized in that aldehydes of the formula XVIII

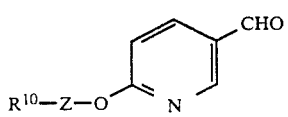
(XVIII)

in which

R¹⁰ and Z have the meanings specified above, are condensed with nitroethane.

17. New compounds of the formula XVIII

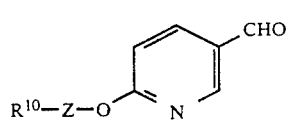
(XVIII)

in which

R¹⁰ and Z have the meanings specified above, where R¹⁰—Z—does not represent methyl.

18. Process for the preparation of the compounds of the formula XVIII according to 17, characterized in that a) alcohols of the formula XIX

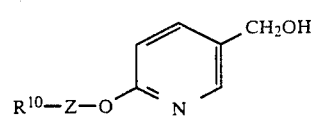
(XIX)

in which

R¹⁰ and Z have the meaning specified under 17, are oxidized, or b) a compound of the formula XXVI

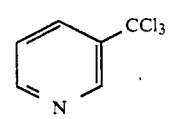
(XXVI)

is reacted with a compound of the formula

R¹⁰—Z—OH  (XXI)

in which R¹⁰ and Z have the meaning specified above, in the presence of bases.

19. New compounds of the formula XIX

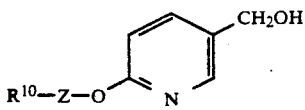 (XIX)

in which
R$^{10}$ and Z have the meanings specified above, and R$^{10}$—Z—does not represent methyl.

20. Process for the preparation of the compounds of the formula XIX mentioned in 19, characterized in that carboxylic acids of the formula XX

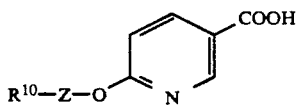 (XX)

in which
R$^{10}$ and Z have the meanings specified above, are reduced.

21. New compounds of the formula XX

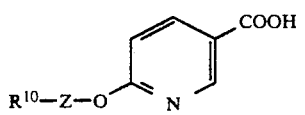 (XX)

in which
R$^{10}$ and Z have the meanings specified above, where R$^{10}$—Z—does not represent methyl.

22. Process for the preparation of the compounds of the formula XX according to 21, characterized in that 6-chloronicotinic acid is reacted with a compound of the formula XXI

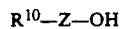 (XXI)

where
R$^{10}$ and Z have the meanings specified above.

23. New compounds of the formula (XXII)

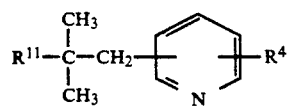 (XXII)

in which
R$^4$ has the meanings specified for the compounds of the formula (I) and the substituents on the pyridyl ring of the formula (XXII) are in the p position with respect to one another, and
R$^{11}$ represents the radicals —NHCHO and

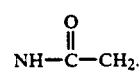

24. Process for the preparation of the compounds of the formula (XXII) according to 23, characterized in that vinyl-substituted pyridines of the formula (XXIII)

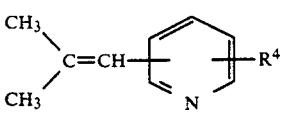 (XXIII)

in which
R$^4$ has the meaning specified for the compounds of the formula (I), and the substituents on the pyridine ring of the formula (XXIII) are in the p position with respect to one another,
are reacted with organic nitriles, alkali metal cyanides or hydrogen cyanide in the presence of organic or inorganic acids.

25. New compounds of the formula (XXIII)

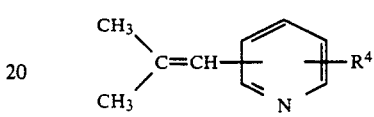 (XXIII)

in which
R$^4$ has the meaning specified for the compounds of the formula (I), and the substituents in the pyridine ring of the formula (XXII) are in the p position with respect to one another.

26. Process for the preparation of the compounds of the formula (XXIII) according to 25, characterized in that pyridines of the formula (XXIV)

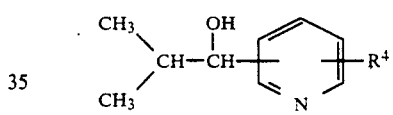 (XXIV)

in which
R$^4$ has the meaning specified for the compounds of the formula (I), and the substituents on the pyridine ring of the formula (XXIV) are in the p position with respect to one another,
a) are reacted in the presence of protonic acids or
b) are reacted initially with a halogenating agent and subsequently with a base.

27. New compounds of the formula (XXIV)

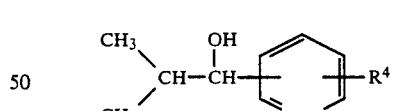 (XXIV)

in which
R$^4$ has the meaning specified for the compounds of the formula (I), and the substituents on the pyridine ring of the formula (XXIV) are in the p position with respect to one another.

28. Process for the preparation of the compounds of the formula (XXIV) according to 27, characterized in that compounds of the formula (XVIII)

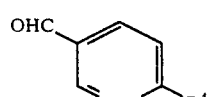 (XVIII)

in which $R^4$ has the meaning specified for the compounds of the formula (I), are reacted with Grignard compounds of the formula (XXV)

in which
Hal represents halogen.

The compounds of the formula I can, when A represents nitrogen, exist in the form of their tautomers. Examples of this are, for the case where $R^2$ represents $NH_2$:

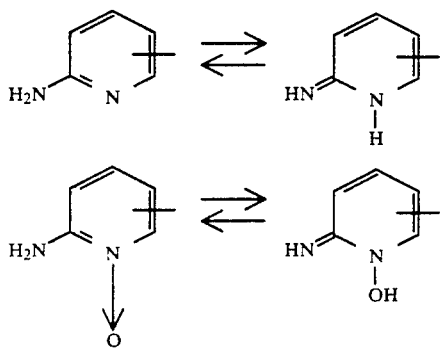

The compounds of the formula I can also exist in the form of their steric and optical isomers and, in this case, form mutually enantiomeric and/or diastereomeric forms.

Physiologically tolerated salts of the compounds of the formula I can be formed with the following acids:

Hydrochloric acid, sulphuric acid, phosphoric acid, perchloric acid, hydrobromic and hydroiodic acid, nitric acid, acetic acid, oxalic acid, malonic acid, succinic acid, ascorbic acid, malic acid, tartaric acid, maleic acid, fumaric acid, methanesulphonic acid, benzoic acid, substituted benzoic acids, formic acid, toluenesulphonic acid, benzenesulphonic acid, phthalic acid, naphthalenesulphonic acid, nicotinic acid, palmitic acid, embonic acid.

Preferred compounds of the formula I are those in which

A represents =CH— or =N—, $R^0$ represents hydrogen or methyl, $R^1$ represents hydrogen, hydroxyl, fluorine, chlorine, bromine, cyano, $C_1$-$C_4$-alkyl, $C_1$-$C_4$-halogenoalkyl, hydroxymethyl, $C_1$-$C_4$-alkoxycarbonyl, aminocarbonyl, mono- or di-$C_1$-$C_4$-alkylaminocarbonyl, $C_1$-$C_6$-alkoxy, $C_1$-$C_6$-halogenoalkoxy, $C_1$-$C_6$-halogenoalkylthio, $NHSO_2$-$C_1$-$C_6$-alkyl, $R^2$ represents hydrogen, hydroxyl, alkoxy or the radical —$NR^5R^6$, $R^3$ represents the radicals specified for $R^1$, $R^4$ represents hydrogen, $C_1$-$C_6$-alkyl which is optionally substituted by hydroxyl, $C_1$-$C_6$-alkoxy, $C_1$-$C_6$-acyloxy or the radical —$NR^7R^8$, and represents the radical $COR^9$ or the radical —O—Z—$R^{10}$, Z represents $C_1$-$C_6$-alkylene, $C_2$-$C_6$-alkenylene or $C_2$-$C_6$-alkynylene $R^5$ represents hydrogen or $C_1$-$C_6$-alkyl, $R^6$ represents hydrogen, $C_1$-$C_6$-alkyl, $C_1$-$C_6$-halogenoalkyl $C_1$-$C_6$-alkylcarbonyl, optionally substituted phenylsulphonyl, $R^7$ represents hydrogen, $C_1$-$C_6$-alkyl, which is optionally substituted, $R^8$ represents the radicals specified for $R^7$, $R^9$ represents hydroxyl, $C_1$-$C_6$-alkoxy or the radical —$NR^7R^8$, $R^{10}$ represents hydroxyl, $C_1$-$C_6$-alkoxy, $C_1$-$C_6$-acyloxy, optionally substituted aryloxy or aralkyloxy, with $R^4$ and the alkylamino group on the pyridine ring of the formula I being in the p position with respect to one another.

Suitable and preferred substituents for the optionally substituted radicals are: cyano, halogen such as fluorine or chlorine, hydroxyl, $C_{1-4}$-alkyl, $C_{1-4}$-halogenoalkyl, phenyl, $C_{1-4}$-alkoxy, $C_{1-4}$-halogenoalkoxy, $C_{1-4}$-alkylthio, $C_{1-4}$-halogenoalkylthio, in the case where the substituents are located on a phenyl radical additionally preferably methylenedioxy, ethylenedioxy, halogen-substituted methylenedioxy, halogen-substituted ethylenedioxy, as well as phenyl, phenoxy, each of which in turn can carry one or more of the abovementioned substituents.

Particularly preferred compounds of the formula I are those in which

A represents =CH— or =N—, $R^0$ represents hydrogen or methyl, $R^1$ represents hydrogen, methyl, ethyl, fluorine, chlorine, bromine, hydroxyl, hydroxymethyl, cyano, methoxy- and ethoxycarbonyl, aminocarbonyl, mono- or di-$C_1$-$C_4$-alkylaminocarbonyl, $C_1$-$C_4$-alkoxy, $C_1$-$C_4$-halogenoalkoxy with 1 to 5 halogen atoms, —$NHSO_2$-$C_1$-$C_4$-alkyl, $R^2$ represents hydrogen, hydroxyl, $C_1$-$C_4$-alkoxy or the radical —$NR^5R^6$, $R^3$ represents the radicals specified for $R^1$, $R^4$ represents hydrogen, $C_1$-$C_3$-alkyl which is preferably substituted by hydroxyl, $C_1$-$C_3$-alkoxy, especially methoxy, $C_1$-$C_3$-acyloxy, especially acetoxy or the radical —$NR^7R^8$, and represents the radical $COR^9$ or the radical —O—Z—$R^{10}$, Z represents $C_1$-$C_4$-alkylene, $C_2$-$C_4$-alkenylene or $C_2$-$C_4$-alkynylene, $R^5$ represents hydrogen or $C_1$-$C_3$-alkyl, especially methyl or ethyl, $R^6$ represents hydrogen, methyl or acetyl, $R^7$ represents hydrogen, $C_1$-$C_3$-alkyl, especially methyl or ethyl, $R^8$ represents hydrogen, $R^9$ represents hydroxyl, $C_1$-$C_3$-alkoxy, especially methoxy or ethoxy, or the radical —$NR^7R^8$, $R^{10}$ represents hydroxyl, $C_1$-$C_3$-alkoxy, especially methoxy or ethoxy, $C_1$-$C_3$-acyloxy, especially acetoxy, optionally substituted aryloxy or aralkyloxy, with $R^4$ and the alkylamino group on the pyridyl ring being in the p position with respect to one another.

Very particularly preferred compounds are those of the following structure in which
A represents =CH— or =NR—
$R^0$ to $R^3$ have the meanings or preferred meanings specified hereinbefore,
$R^4$ represents the radical —O—Z—$R^{10}$ where Z and $R^{10}$ have the preferred meanings specified hereinbefore. Besides the examples, specific mention may be made of the following compounds of the formula I:
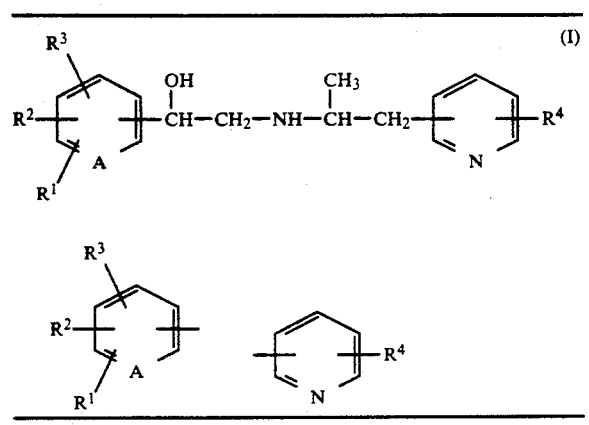
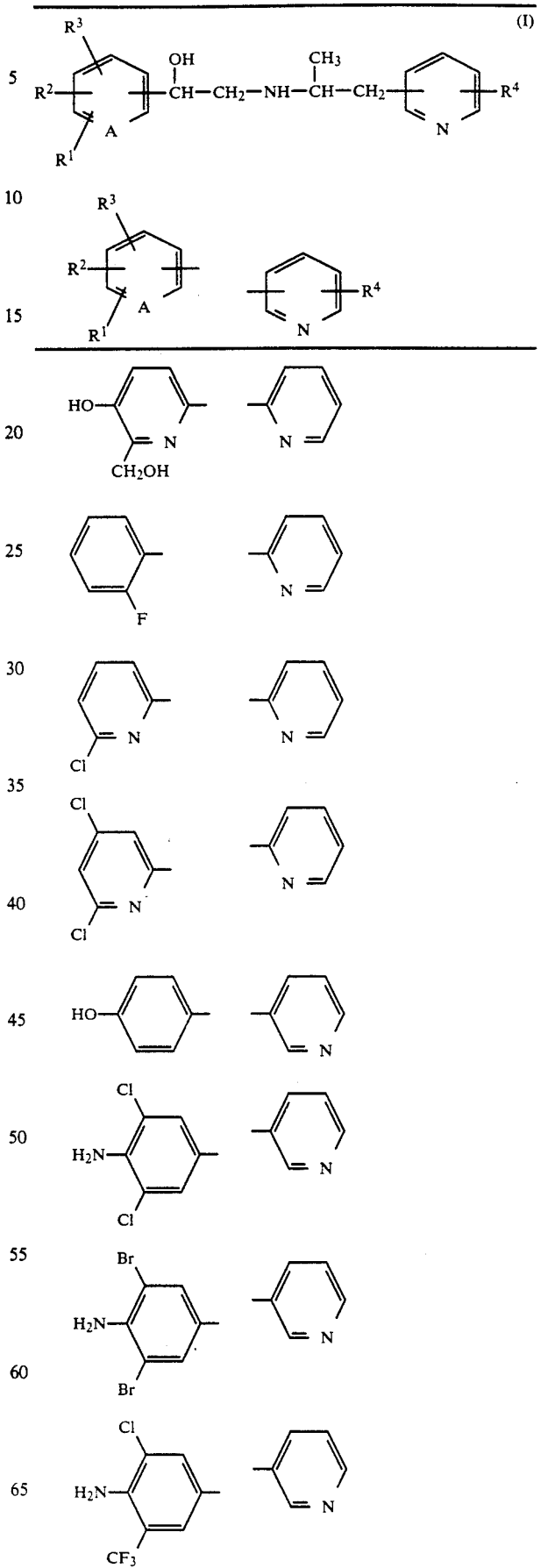

-continued
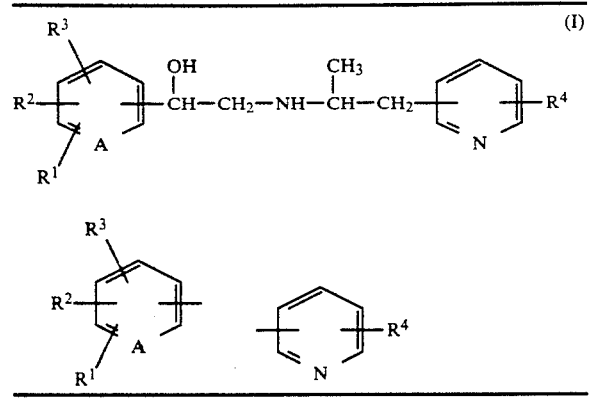
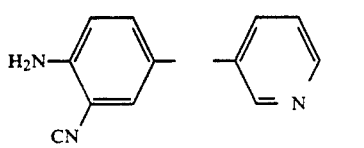
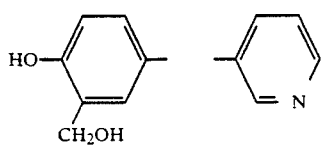
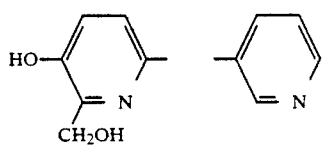
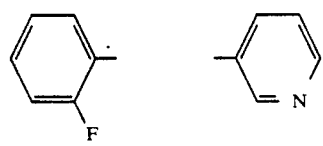
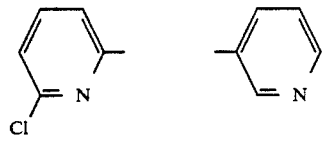
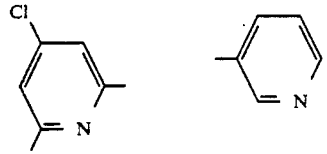
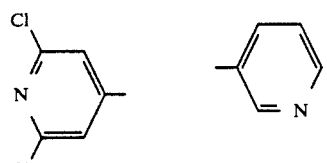
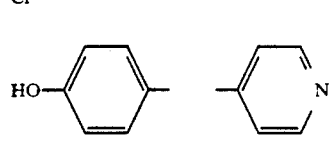
-continued
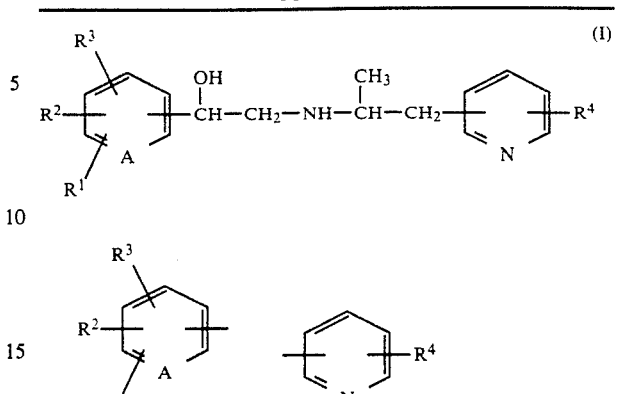
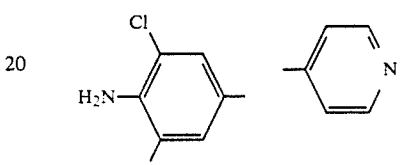
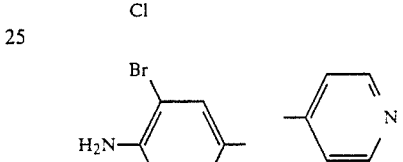
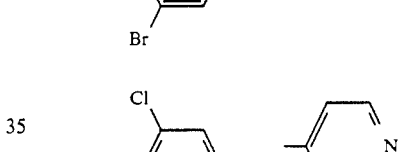
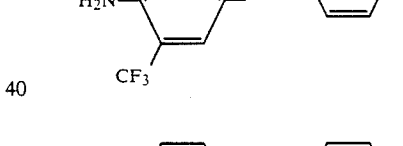
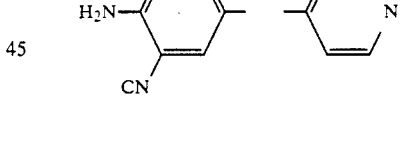
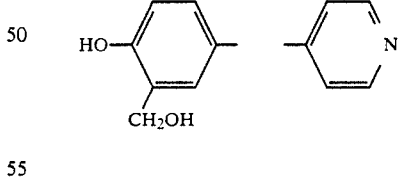
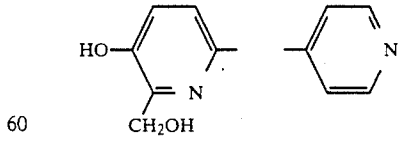
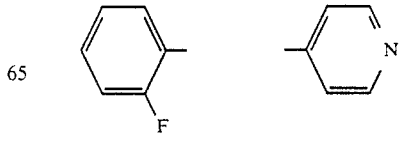

-continued
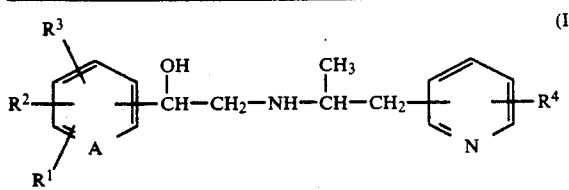
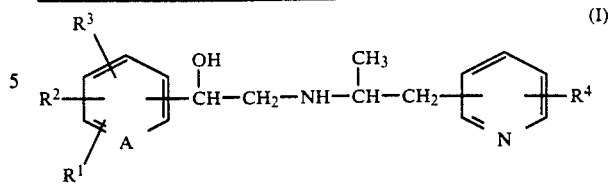
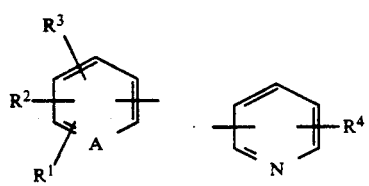
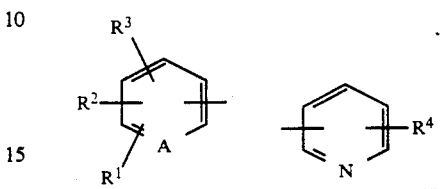
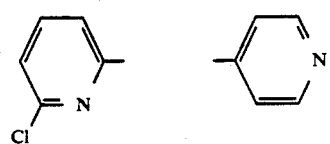
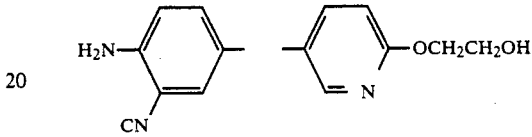
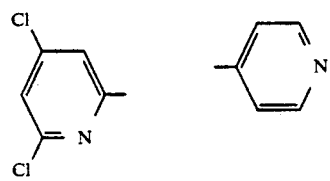
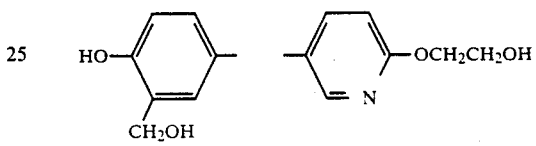
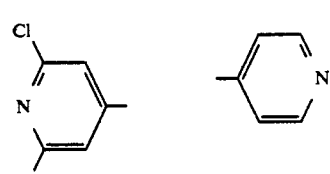
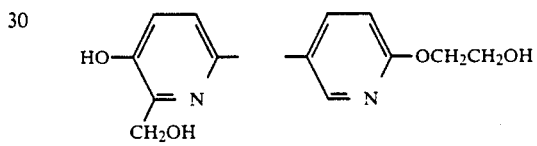
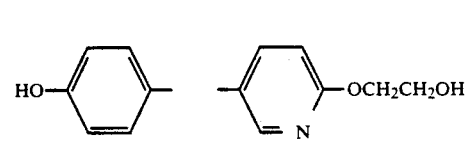
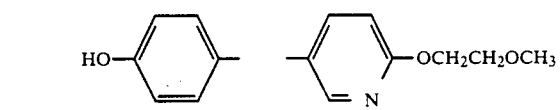
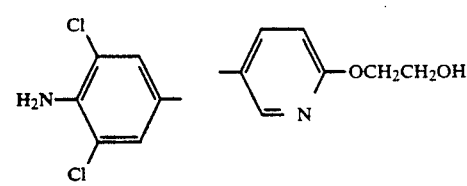
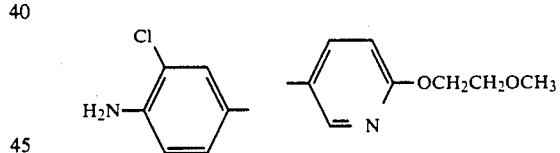
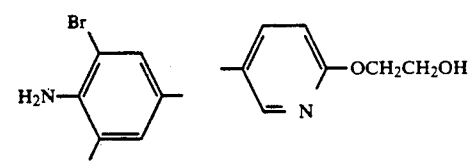
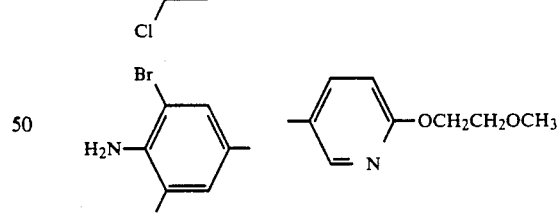
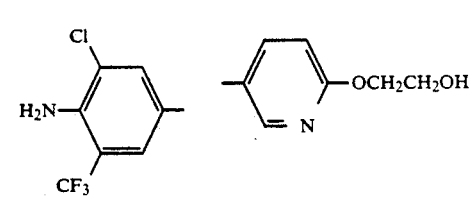
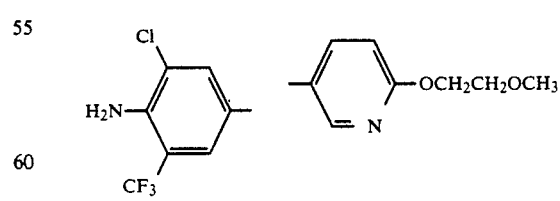
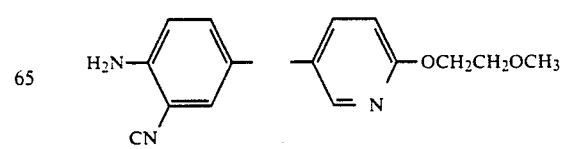

-continued
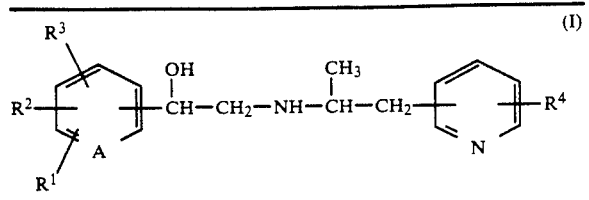
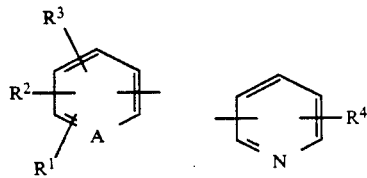
| | |
|---|---|
| 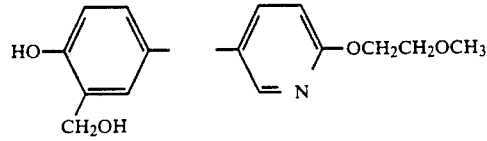 | |
| 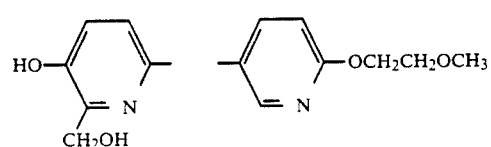 | |
| 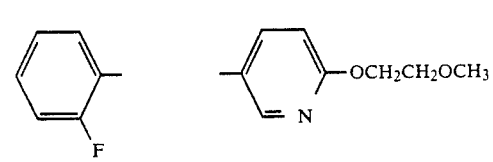 | |
| 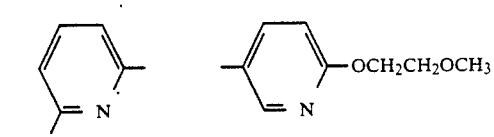 | |
| 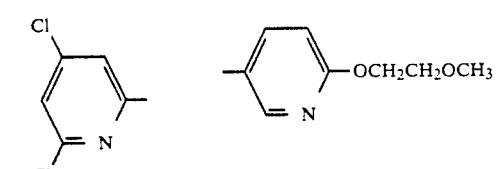 | |
| 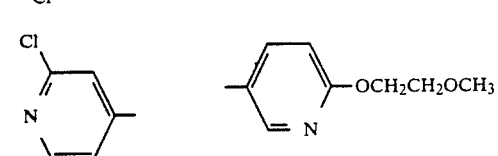 | |
| 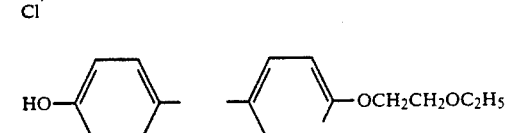 | |
| 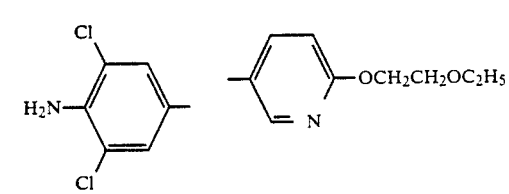 | |
-continued
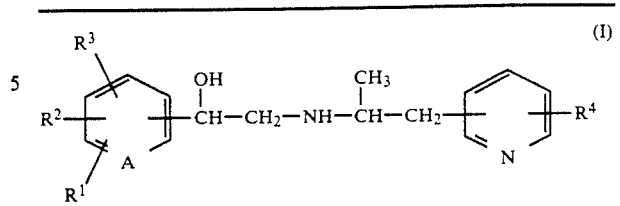
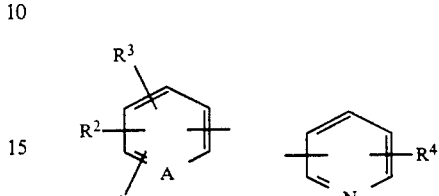
| | |
|---|---|
| 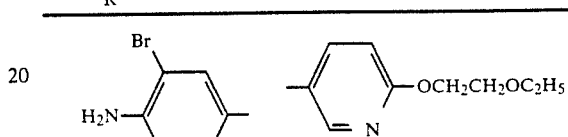 | |
| 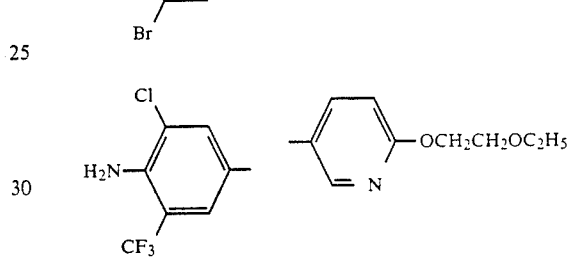 | |
| 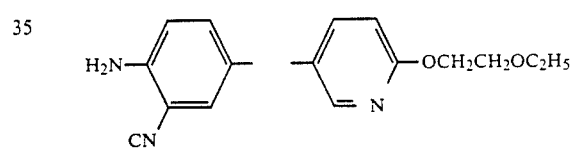 | |
| 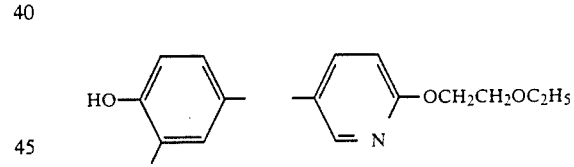 | |
| 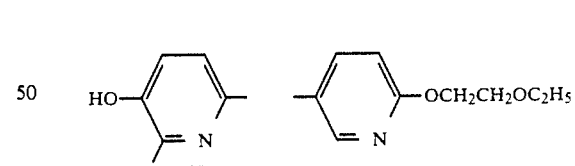 | |
| 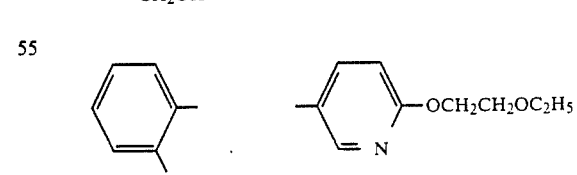 | |
| 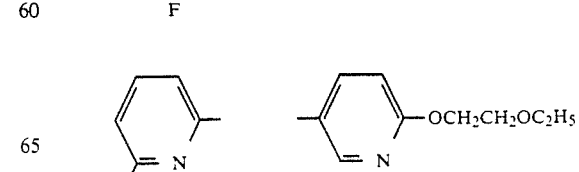 | |
|  | |

-continued
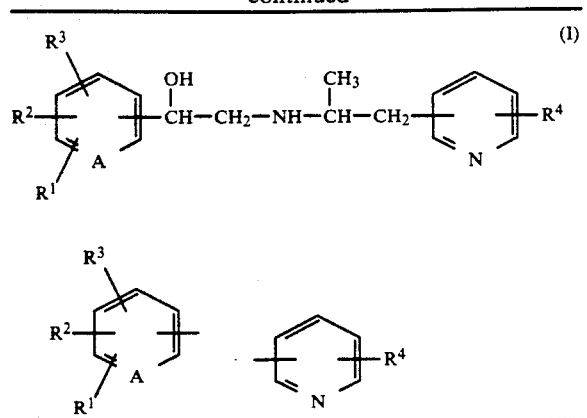
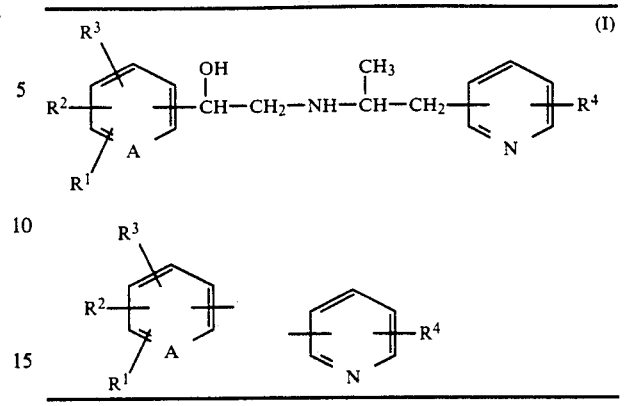
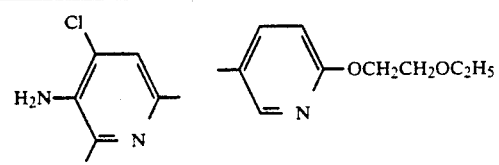
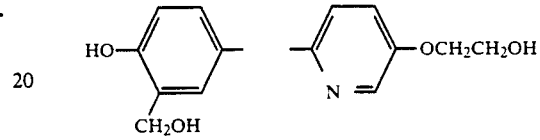
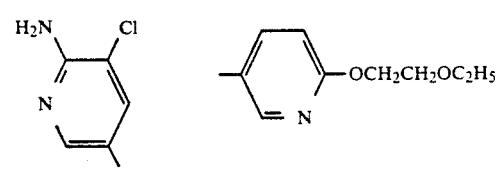
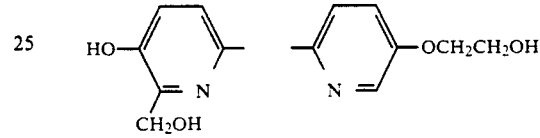
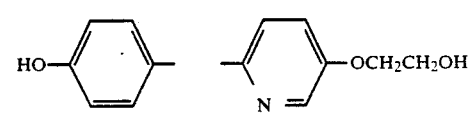
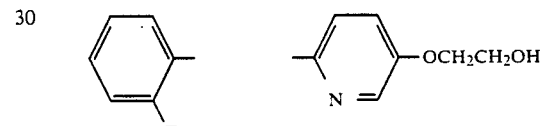
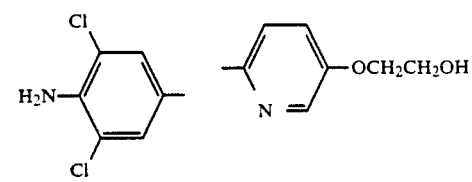
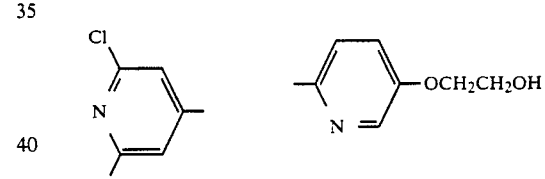
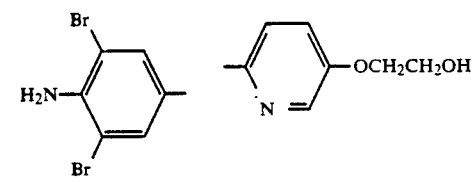
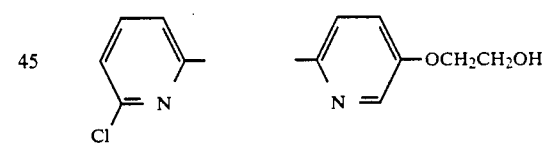
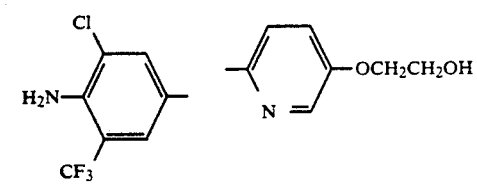
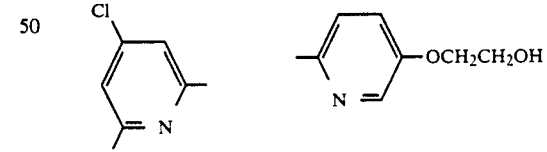
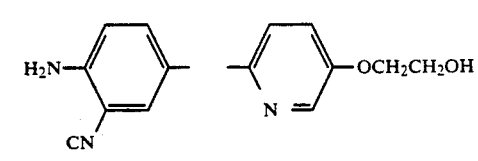
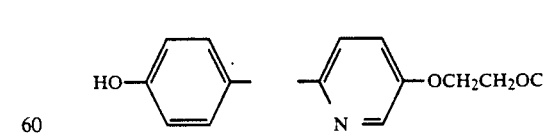
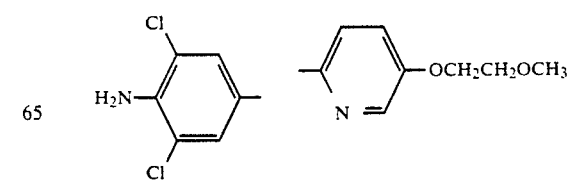

-continued
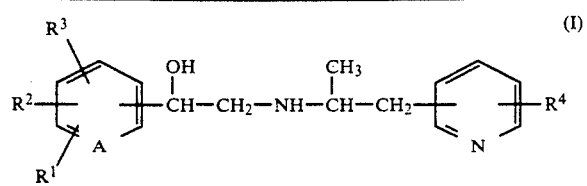
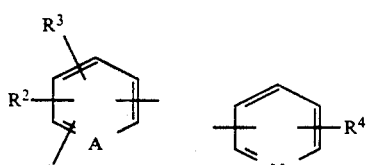
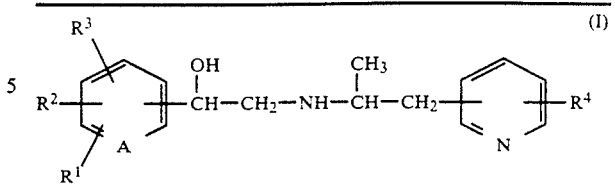
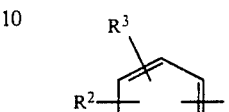
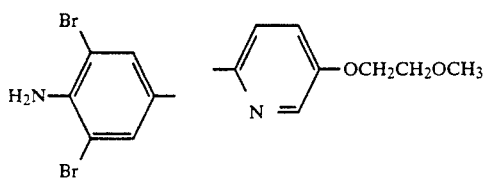
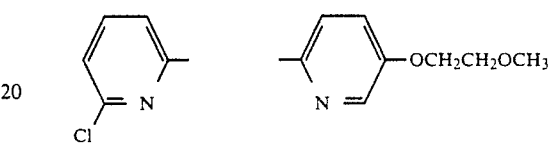
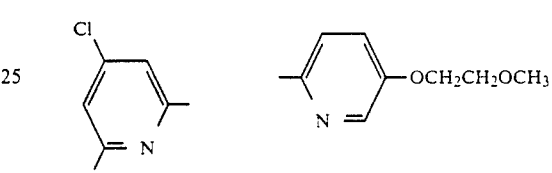
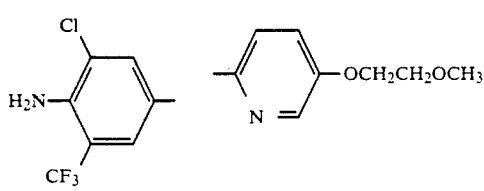
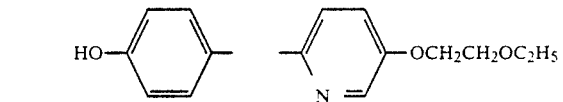
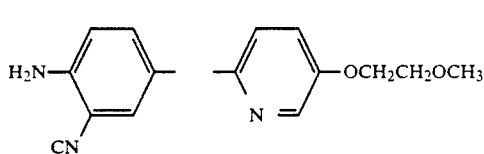
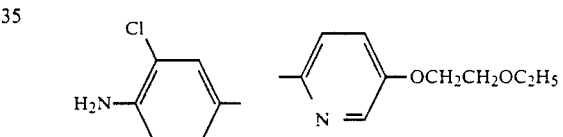
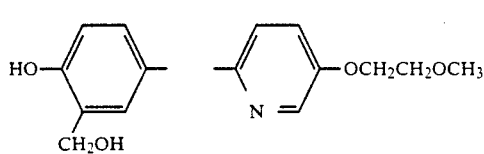
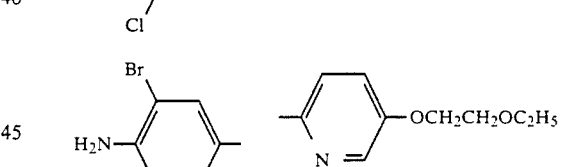
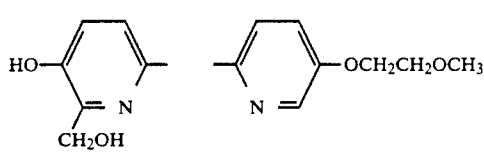
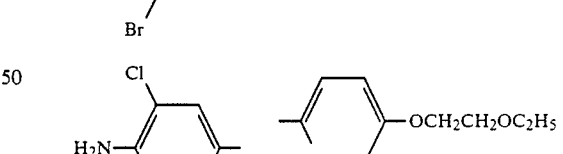
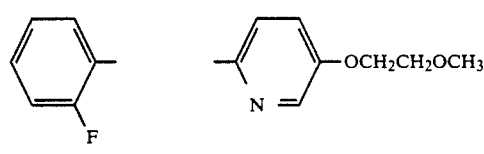
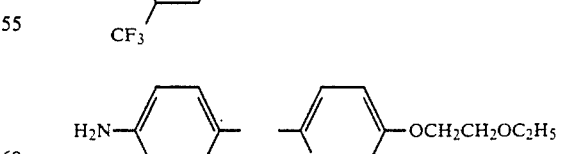
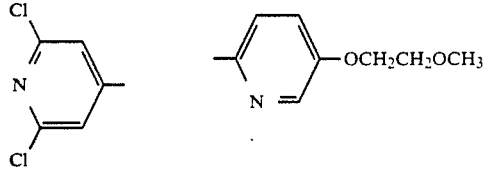
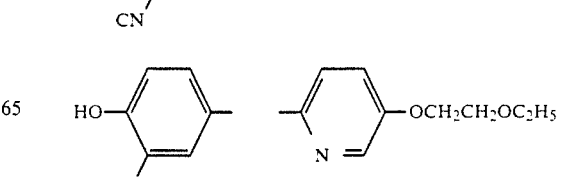

-continued
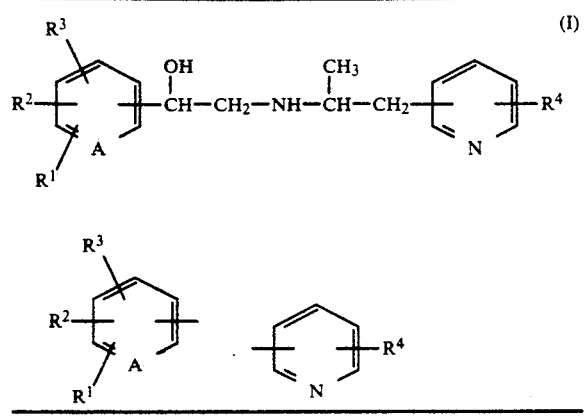
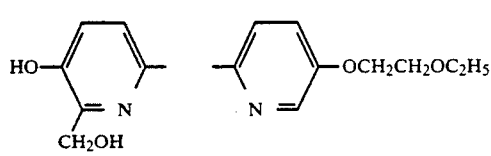
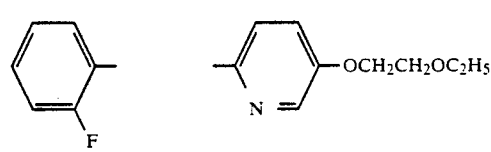
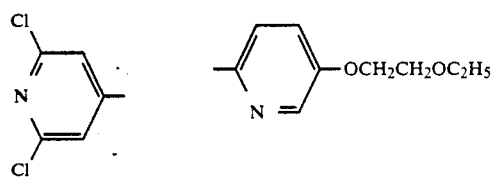
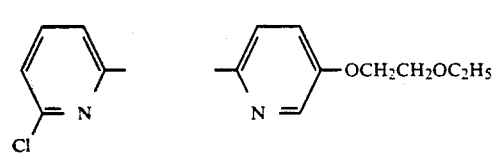
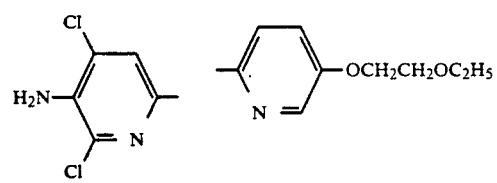
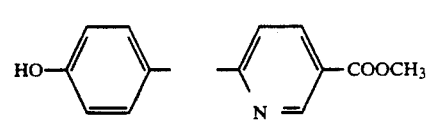
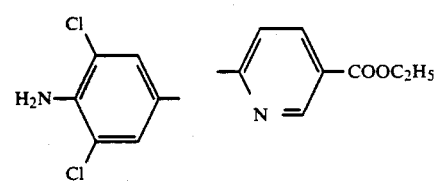
-continued
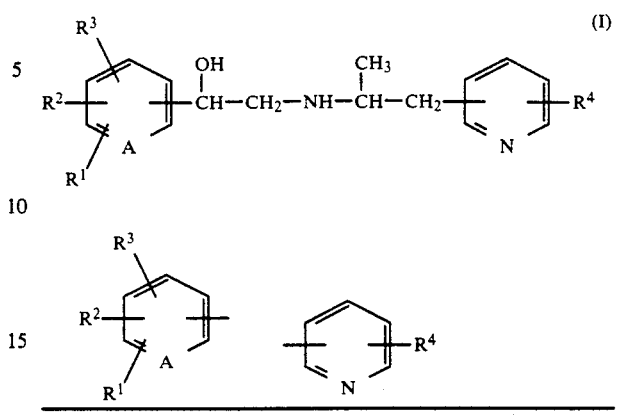
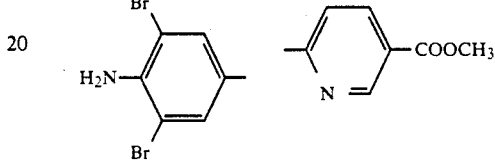
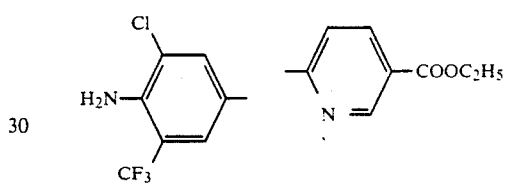
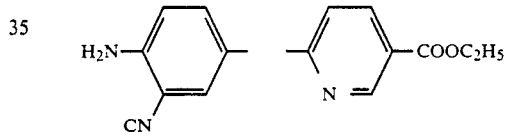
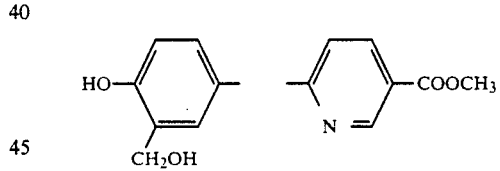
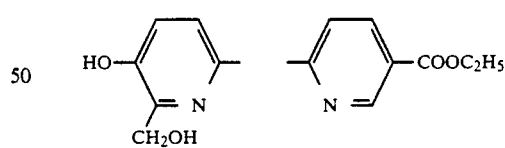
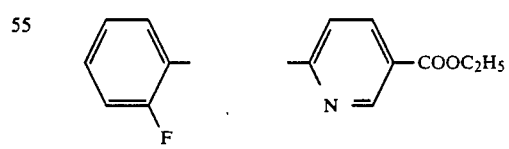
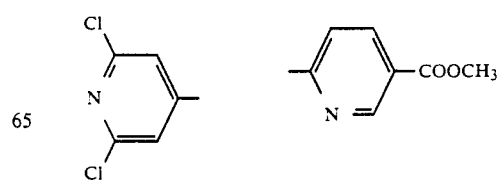

-continued
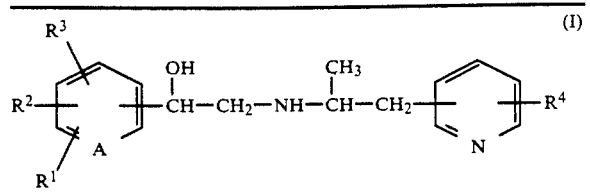
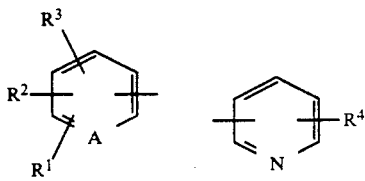
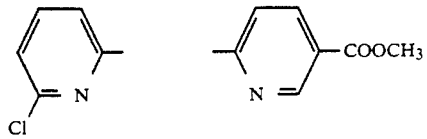
Furthermore, besides the examples, mention may be made of the following compounds of the formula I;
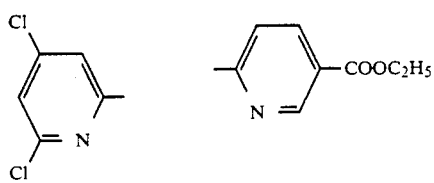
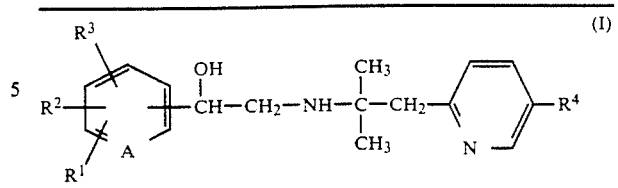
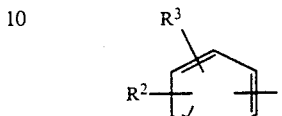
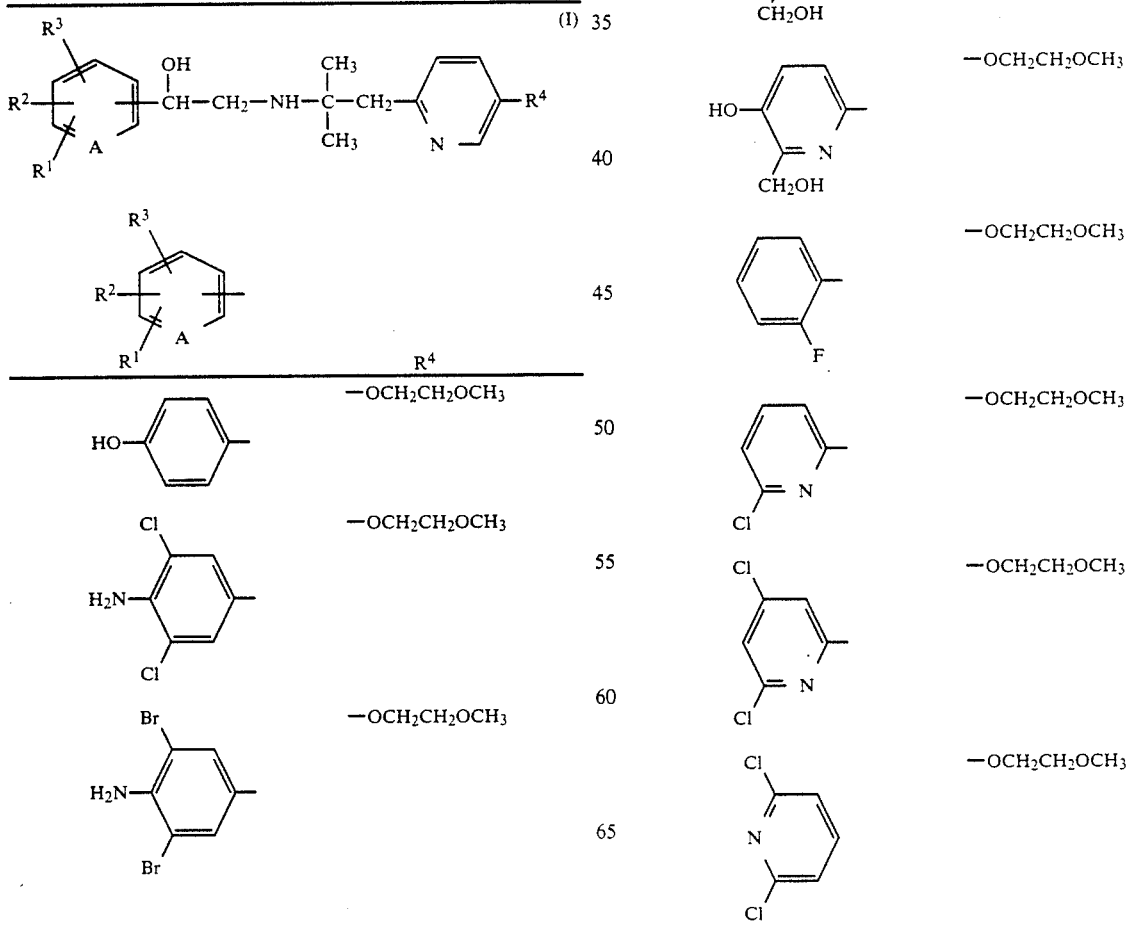

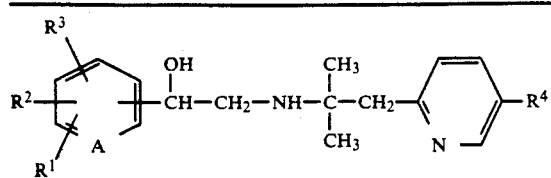 (I)

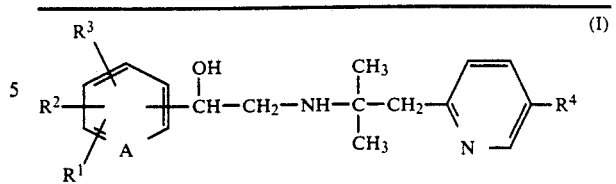 (I)

| | R⁴ |
|---|---|
| 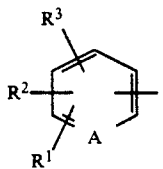 | —OCH₂CH₂OC₂H₅ |
| 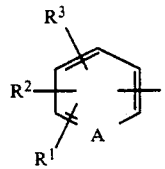 | —OCH₂CH₂OC₂H₅ |
| 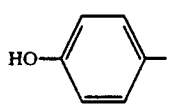 | —OCH₂CH₂OC₂H₅ |
| 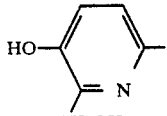 | —OCH₂CH₂OC₂H₅ |
| 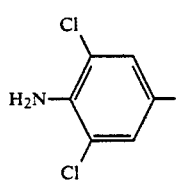 | —OCH₂CH₂OC₂H₅ |
| 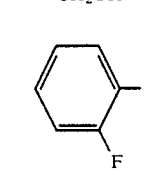 | —OCH₂CH₂OC₂H₅ |
| 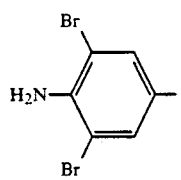 | —OCH₂CH₂OC₂H₅ |
| 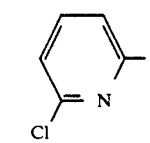 | —OCH₂CH₂OC₂H₅ |
| 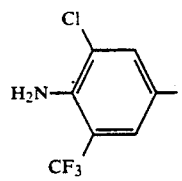 | —OCH₂CH₂OC₂H₅ |
| 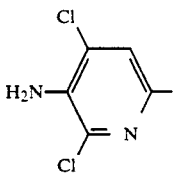 | —OCH₂CH₂OC₂H₅ |
| 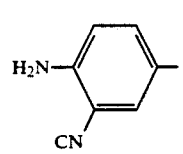 | —OCH₂CH₂OC₂H₅ |
| 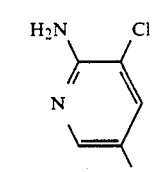 | —OCH₂CH₂OC₂H₅ |

The salts with hydrochloric acid, sulphuric acid, oxalic acid, maleic acid, fumaric acid, malonic acid, benzoic acid may be mentioned as preferred.

The compounds of the formula (I) can be prepared by processes a) to f) specified above under 2.

When, in process 2a), 2-fluoro-3-bromoacetylbenzene is used as halogenomethyl ketone of the formula (II), and -(5-methoxycarbonyl-2-pyridyl)-2-propylamine is used as amine of the formula (III), process a) can be depicted by the following reaction scheme:

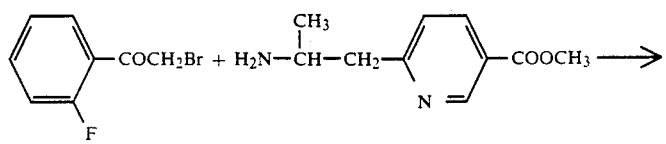

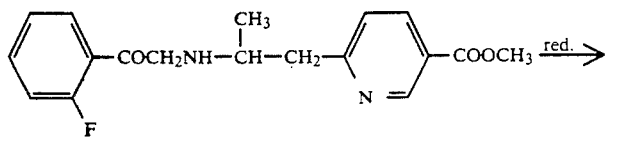

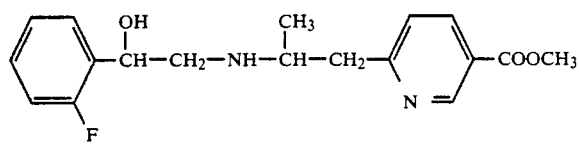

Compounds of the formula (II) are known (compare, for example, DE-OS (German Published Specification) 3,615,293, U.S. Pat. No. 4,522,822, European Published Specification 23,385). The substituents $R^1$, $R^2$, $R^3$ and A in formula (II) preferably have the meanings specified hereinbefore as preferred. The following specific compounds of the formula (II) may be mentioned:

2-Amino-3-chloro-5-pyridyl chloromethyl ketone,
2-Amino-3-cyano-5-pyridyl chloromethyl ketone,
2,4-Dichloro-3-amino-6-pyridyl bromomethyl ketone,
2-Cyano-3-amino-6-pyridyl bromomethyl ketone,
3-Amino-4-cyano-6-pyridyl bromomethyl ketone,
3-Amino-4-cyano-6-pyridyl chloromethyl ketone,
2-Cyano-3-amino-4-chloro-6-pyridyl bromomethyl ketone,
2-Cyano-3-amino-4-chloro-6-pyridyl chloromethyl ketone,
2-Chloro-3-amino-4-trifluoromethyl-6-pyridyl bromomethyl ketone,
2-Trifluoromethyl-3-amino-4-cyano-6-pyridyl bromomethyl ketone,
2-Fluoro-3-amino-4-cyano-6-pyridyl chloromethyl ketone,
4-Amino-3,5-dichlorophenyl bromomethyl ketone,
4-Amino-3-chloro-5-trifluoromethylphenyl bromomethyl ketone,
4-Amino-3-cyanophenyl bromomethyl ketone,
6-Chloro-2-pyridyl bromomethyl ketone,
4,6-Dichloro-2-pyridyl bromomethyl ketone,
2,6-Dichloro-4-pyridyl bromomethyl ketone,
3-Chlorophenyl bromomethyl ketone.

Amines of the formula (III) are new when $R^4$ does not represent hydrogen. The preparation thereof is described hereinafter. $R^0$ and $R^4$ preferably have the meanings specified for the compounds of the formula (I). The following specific compounds of the formula (III) may be mentioned:

1-[2-(2-Hydroxyethoxy)-5-pyridyl]-2-aminopropane
1-[2-(2-Methoxyethoxy)-5-pyridyl]-2-aminopropane
1-[2-(2-Ethoxyethoxy)-5-pyridyl]-2-aminopropane
1-[2-Ethoxycarbonyl-5-pyridyl)-2-aminopropane
1-[5-(2-Hydroxyethoxy)-2-pyridyl]-2-aminopropane
1-[5-(2-Methoxyethoxy)-2-pyridyl]-2-aminopropane
1-[5-(2-Ethoxyethoxy)-2-pyridyl]-2-aminopropane
1-[2-(2-Methoxyethoxy)-5-pyridyl]-2-amino-2-methylpropane
1-[2-(2-Ethoxyethoxy) idyl]-2-amino-2-methylpropane.

The following reducing agents may be mentioned as reducing agents for carrying out process 2a):

$H_2$/catalyst, the following may be mentioned as examples of the catalyst: $PtO_2$, Pd-active charcoal; complex metal hydrides such as, for example $LiAlH_4$, $NaBH_4$, $NaBH_3CN$.

The following reducing agents are particularly preferably employed:

$NaBH_4$ and $NaBH_3CN$

Process 2a) is carried out by mixing compounds (II) and (III) in a diluent in approximately equimolar ratio.

The reaction is preferably carried out at temperatures from $-20°$ C. to $+100°$ C.

It is preferably carried out under atmospheric pressure.

All inert organic solvents are used as diluents. These include, in particular, aliphatic and aromatic hydrocarbons such as pentane, hexane, cyclohexane, petroleum ether, ligroin, benzene, toluene; chlorinated hydrocarbons such as methylene chloride, ethylene chloride, chloroform; ethers such as diethyl ether and glycol dimethyl ether; nitriles such as acetonitrile, propionitrile and benzonitrile; alcohols such as methanol, ethanol, n- and i-propanol.

Alcohols are preferred, in which case the reduction can be carried out immediately without isolating the intermediates.

When, in process 2b), 3-chlorophenyl epoxide is used as epoxide of the formula (IV), and 1-[5-(2-methoxyethoxy)-2-pyridyl]-2-aminopropane is used as amine of the formula (III), process 2b) can be depicted by the following reaction scheme:

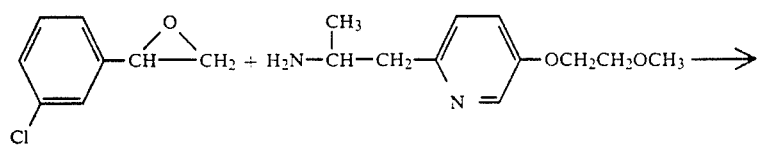

-continued

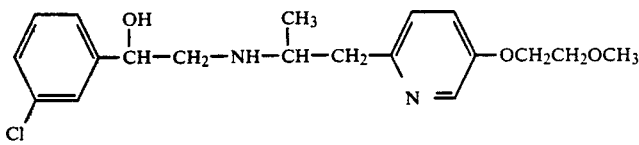

Epoxides of the formula (IV) are known (compare, for example, DE-OS (German Published Specification) 3,615,293; U.S. Pat. No. 4,522,822; EP 23,385). The aminopropane is used as amine of the formula (III), process c) can be depicted by the following reaction scheme:

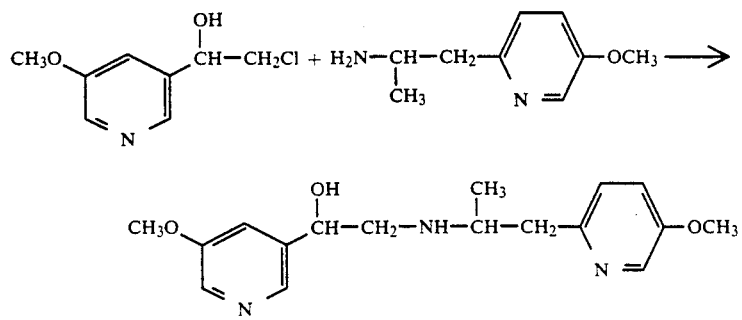

substituents $R^1$, $R^2$, $R^3$ and A preferably have the meanings specified hereinbefore as preferred. The following specific epoxides may be mentioned:
2-Amino-3-chloropyridine-5-epoxide,
2-Amino-3-cyanopyridine-5-epoxide,
2,4-Dichloro-3-aminopyridine-6-epoxide,
2-Chloro-3-amino-4-cyanopyridine-6-epoxide,
2-Cyano-3-amino-4-chloropyridine-6-epoxide,
2-Cyano-3-aminopyridine-6-epoxide,
2-Chloro-3-amino-4-trifluoromethylpyridine-6-epoxide,
2-Bromo-3-amino-4-cyanopyridine-6-epoxide,
4-Amino-3,5-dichlorophenyl-epoxide,
4-Amino-3-chloro-5-trifluoromethylphenyl-epoxide,
4-Amino-3-cyanophenyl-epoxide,
2-Chloropyridine-6-epoxide,
2,4-Dichloropyridine-6-epoxide,
2,6-Dichloropyridine-4-epoxide, Process 2b) is carried out by reacting approximately equimolar amounts of the epoxide of the formula IV and of the amine of the formula (III) in a diluent.

In general, an excess of amine (1-3 molar), preferably 1-1.5 molar) relative to the epoxide of the formula (IV) is used.

The reaction is preferably carried out at temperatures from +20° C. to +150° C.

It is preferably carried out under atmospheric pressure.

All inert organic solvents are used as diluents. These include, in particular, aliphatic and aromatic, optionally halogenated hydrocarbons, such as pentane, hexane, heptane, cyclohexane, petroleum ether, petroleum spirit, ligroin, benzene, toluene, methylene chloride, ethylene chloride, chloroform, carbon tetrachloride, chlorobenzene and o-dichlorobenzene, as well as ethers such as diethyl and dibutyl ether, glycol dimethyl ether and diglycol dimethyl ether, tetrahydrofuran and dioxane, as well as nitriles such as acetonitrile and benzonitrile, amides such as dimethylformamide, alcohols such as methanol, ethanol, n- and i-propanol.

Alcohols are preferred.

When, in process 2c), 5-methoxy-3-(1-hydroxy-2-chloroethyl)pyridine is used as β-halogenomethyl compound of the formula V, and 1-(5-methoxy-2-pyridyl)-2-

β-halogenoethyl compounds of the formula (V) are known (compare, for example, DE-OS (German Published Specification) 3,615,293, U.S. Pat. No. 4,522,822, EP 23,385).

The substituents $R^1$, $R^2$, $R^3$ and A in formula (II) preferably have the meanings specified as preferred for the compounds of the formula (I).

The following specific compounds of the formula (V) may be mentioned:
1-(2-Amino-3-chloro-5-pyridyl)-2-chloroethanol,
1-(2-Amino-3-cyano-5-pyridyl)chloroethanol,
1-(2,4-Dichloro-3-amino-6-pyridyl)-2-chloroethanol,
1-(2-Chloro-3-amino-4-cyano-6-pyridyl)chloroethanol,
1-(2-Cyano-3-amino-4-chloro-6-pyridyl)bromomethanol,
1-(2-Cyano-3-amino-6-pyridyl)-2-chloroethanol,
1-(3-Amino-4-cyano-6-pyridyl)-2-bromoethanol,
1-(2-Chloro-3-amino-4-trifluoromethyl-6-pyridyl)-2-chloroethanol,
1-(4-Amino-3,5-dichlorophenyl)-2-bromoethanol,
1-(4-Amino-3-chloro-5-trifluoromethylphenyl)-2-chloroethanol,
1-(4-Amino-3-cyanophenyl)-2-bromoethanol,
1-(6-Chloro-2-pyridyl)-2-bromoethanol,
1-(4,6-Dichloro-2-pyridyl)-2-bromoethanol,
1-(2,6-Dichloro-4-pyridyl)-2-bromoethanol,
1-(3-Chlorophenyl)-2-bromoethanol,
1-(2-Fluorophenyl)-2-bromoethanol.

Process 2c) is carried out by reacting the beta-halogenoethyl compound of the formula V with excess amine of the formula (III), where appropriate in the presence of a diluent.

The reaction is carried out at temperatures from +20° to +150° C.

It is carried out under atmospheric pressure or under elevated pressure.

All inert organic solvents are used as diluents. These include, in particular, aliphatic and aromatic, optionally halogenated hydrocarbons such as pentane, hexane, cyclohexane, benzene, toluene, methylene chloride, chloroform, as well as ethers such as diethyl ether, tetrahydrofuran and dioxane, furthermore nitriles such as acetonitrile and benzonitrile, as well as amides such as dimethylformamide, as well alcohols such as methanol, ethanol, n- and i-propanol.

Alcohols are preferably used.

When, in process 2d), 1-(5-fluoro-3-pyridyl)-2-aminoethanol is used as compound of the formula VI, and (5-methoxy-2-pyridyl)acetone is used as compound of the formula (VII), the process can be depicted by the following formula diagram:

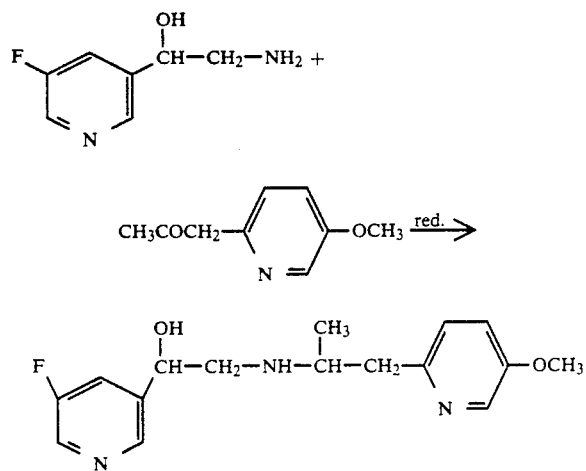

Compounds of the formula (VI) are known (compare, for example, DE-OS (German Published Specification) 3,615,293, U.S. Pat. No. 4,522,822, EP 23,385, DE-OS (German Published Specification) 3,627,663). The substituents $R^1$, $R^2$, $R^3$ and A in formula (II) preferably have the meanings specified as preferred for the compounds of the formula (I).

The following specific compounds of the formula (VI) may be mentioned:
1-(2-Amino-3-chloro-5-pyridyl)-2-aminoethanol,
1-(2-Amino-3-cyano-5-pyridyl)-2-aminoethanol,
1-(2,4-Dichloro-3-amino-6-pyridyl)-2-aminoethanol,
1-(2-Chloro-3-amino-4-cyano-6-pyridyl)-2-aminoethanol,
1-(2-Cyano-3-amino-6-pyridyl)aminoethanol,
1-(2-Chloro-3-amino-4-trifluoromethyl-6-pyridyl)-2-aminoethanol,
1-(4-Amino-3,5-dichlorophenyl)-2-aminoethanol,
1-(4-Amino-3-chloro-5-trifluoromethylphenyl)-2-aminoethanol,
1-(4-Amino-3-cyanophenyl)-2-aminoethanol,
1-(6-Chloro-2-pyridyl)-2-aminoethanol,
1-(4,6-Dichloro-2-pyridyl)-2-aminoethanol,
1-(2,6-Dichloro-4-pyridyl)-2-aminoethanol,
1-(3-Chlorophenyl)-2-aminoethanol,
1-(2-Fluorophenyl)-2-aminoethanol.

Some of the compounds of the formula (VII) are new. The preparation of the new compounds is described hereinafter. The radical $R^4$ preferably has the meanings specified as preferred hereinbefore. The following specific compounds of the formula (VII) may be mentioned.
[5-(2-Hydroxyethoxy)-2-pyridyl]acetone,
[5-(2-Methoxyethoxy)-2-pyridyl]acetone,
[5-(2-EthoxyethOxy)-2-pyridyl]a cetone,
(5-Ethoxycarbonyl-2-pyridyl]acetone,
[2-(2-Hydroxyethoxy)-5-pyridyl]acetone,
[2-(2-Methoxyethoxy)-5-pyridyl]acetone,
[2-(2-Ethoxyethoxy)-5-pyridyl]acetone.

Process 2d) is carried out by introducing approximately equimolar amounts of the compounds of the formulae (VI) and (VII) into a diluent and reducing the mixture.

The reaction is carried out at temperatures from 0° C. to 150° C.

It is preferably carried out under atmospheric pressure.

All inert organic solvents are used as diluents. These include aliphatic and aromatic, optionally halogenated hydrocarbons such as pentane, hexane, cyclohexane, benzene, toluene, methylene chloride, chloroform, chlorobenzene, as well as ethers such as diethyl ether, tetrahydrofuran, dioxane, furthermore nitriles such as acetonitrile and benzonitrile, as well as amides such as dimethylformamide, as well as alcohols such as methanol, ethanol.

The following are used as reducing agents: $H_2$/catalyst, $PtO_2$ may be mentioned as an example of the catalyst; complex metal hydrides such as, for example, $LiAlH_4$, $NaBH_3CN$.

When, in process 2e), 2-fluorophenylglyoxal is used as compound of the formula (VIII), and 1-[5-(2-methoxyethoxy)-2-pyridyl]-2-aminopropane is used as amine of the formula (III), the process can be depicted by the following reaction scheme:

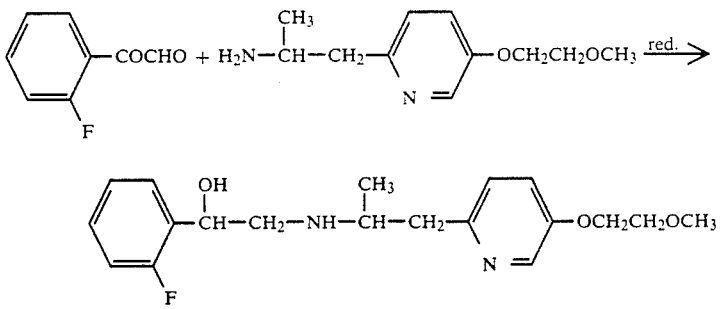

Compunds of the formula (VIII) are known (compare, for example, DE-OS (German Published Specification) 3,615,293, U.S. Pat. No. 4,522,822, EP 23,385). The substituents $R^1$, $R^2$, $R^3$ and A informula (VIII) preferably have the meanings specified hereinbefore as preferred for the compounds of the fomula (I). The following specific compounds of the formula (VIII) may be mentioned:
2-Amino-3-chloro-5-pyridylglyoxal,
2-Amino-3-cyano-5-pyridylglyoxal,
2,4-Dichloro-3-amino-6-pyridylglyoxal,
2-Cyano-3-amino-6-pyridylglyoxal,
2-Chloro-3-amino-4-trifluoromethyl-6-pyridylglyoxal,
4-Amino-3,5-dichloro-phenylglyoxal, 4-Amino-3-chloro-5-trifluoromethyl-phenylglyoxal,
4-Amino-3-cyano-phenylglyoxal,
6-Chloro-2-pyridylglyoxal,
4,6-Dichloro-2-pyridylglyoxal,
2,6-Dichloro-4-pyridylglyoxal,
3-Chloro-phenylglyoxal,
2-Fluoro-phenylglyoxal.

Process 2e) is carried out by adding to the compound of the formula (VIII) in a diluent approximately the equivalent amount of the amine of the formula (III) and subsequently reducing.

The reaction is carried out at temperatures from 0° C. to 100° C.

It is preferably carried out under atmospheric pressure.

All inert organic solvents are used as diluents. These include, in particular, aliphatic and aromatic hydrocarbons such as pentane, hexane, heptane, cyclohexane, petroleum ether, petroleum spirit, ligroin, benzene, toluene, methylene chloride, ethylene chloride, chloroform, carbon tetrachloride, chlorobenzene and o-dichlorobenzene, as well as ethers such as diethyl and dibutyl ether, glycol dimethyl ether and diglycol dimethyl ether, tetrahydrofuran and dioxane, additionally esters such as methyl and ethyl acetate, as well as nitriles such as, for example, acetonitrile and propionitrile, benzonitrile, furthermore amides such as, for example, dimethylformamide, dimethylacetamide and N-methylpyrrolidone, plus tetramethylene sulfone and hexamethylphosphoric triamide, furthermore alcohols such as methanol, ethanol, n- and i-propanol.

H2/catalyst are used as reducing agents; PtO2 and Pd-carbon may be mentioned as catalyst, as well as complex metal hydrides such as LiAlH4 and NaBH4.

When, in process 2f), the 2-[3-(5-methoxy-2-pyridyl)]-propylamide of 3-chloromandelic acid is used as compound of the formula (IX), the process can be depicted by the following formula diagram:

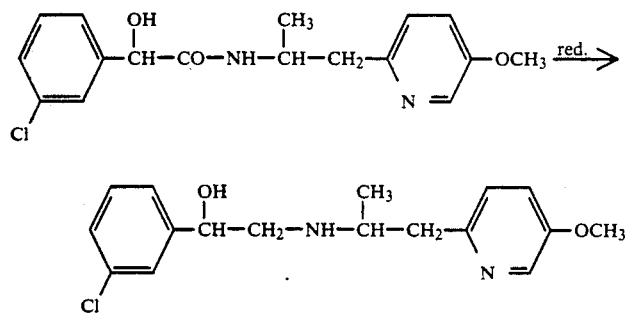

Compounds of the formula (IX) are new. The preparation thereof is described hereinafter. The substituents $R^0$ to $R^4$ and A preferably have the meanings specified hereinbefore as preferred for the compounds of the formula (I). The following specific compounds may be mentioned:

2-[3-[5-(2-Methoxyethoxy)]-2-pyridylpropylamide of 3-chloromandelic acid,
2-[3-[5-(2-Methoxyethoxy)]-2-pyridyl]propylamide of 2-fluoromandelic acid,
2-[3-[5-(2-Methoxyethoxy)]-2-pyridyl]propylamide of (6-chloro-2-pyridyl)hydroxyacetic acid,
2-[3-[5-(2-Ethoxyethoxy)]-2-pyridyl]propylamide of (4,6-dichloro-2-pyridyl)hydroxyacetic acid,
2-[3-[5-(2-Methoxyethoxy)]-2-pyridyl]propylamide of (2,6-dichloro-4-pyridyl)hydroxyacetic acid,
2-[3-[-(2-Methoxyethoxy)]-5-pyridyl]propylamide of 3-chloromandelic acid,
2-[3-[2-(2-Ethoxyethoxy)]-5-pyridyl]propylamide of (6-chloro-2-pyridyl)hydroxyacetic acid.

Process 2f) is carried out by reacting the compound of the formula (IX) in a diluent with excess reducing agent.

The reaction is carried out at temperatures from 0° C. to +150° C.

It is preferably carried out under atmospheric pressure.

All inert organic solvents are used as diluents. These include, in particular, aliphatic and aromatic, optionally halogenated hydrocarbons such as pentane, hexane, heptane, cyclohexane, petroleum ether, petroleum spirit, ligroin, benzene, toluene, methylene chloride, ethylene chloride, chloroform, carbon tetrachloride, chlorobenzene and o-dichlorobenzene, as well as ethers such as diethyl and dibutyl ether, glycol dimethyl ether and diglycol dimethyl ether, tetrahydrofuran and dioxane.

Complex metal hydrides such as LiAlH4, boranes such as diborane, are used as reducing agents.

When, in process 4 a, (2-methoxy-5-pyridyl)acetone is used as compound of the formula (VII), the process can be depicted by the following reaction scheme:

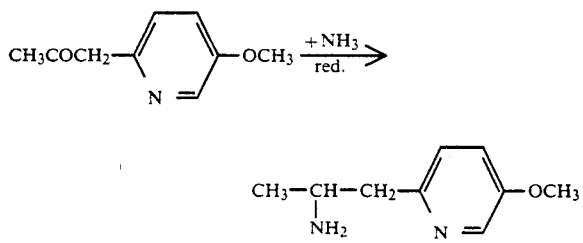

Some of the compounds of the formula (VII) are new. The preparation of the new compounds is described hereinafter. The substituent $R^4$ preferably has the meanings mentioned hereinbefore as preferred for the compounds of the formula (I) and is in the p-position with respect to the acetonyl group. The following specific compounds of the formula (VII) may be mentioned:

[5-(2-Hydroxyethoxy)-2-pyridyl]acetone,
[5-(2-Methoxyethoxy)-2-pyridyl]acetone,
15-(2-Ethoxyethoxy)-2-pyridyl]acetone,
(5-Ethoxycarbonyl-2-pyridyl)acetone,
[2-(2-Hydroxyethoxy)-5-pyridyl]acetone,
[2-(2-Methoxyethoxy)-5-pyridyl]acetone,

[2-(2-Ethoxyethoxy)-5-pyridyl]acetone.

The process is carried out by, in a manner known per se, a) catalytically reducing a compound of the formula (VII) in the presence of excess ammonia (compare Houben-Weyl, Methoden der org. Chemie. (Methods of Org. Chemistry), Vol. 11/1, pages 602 et seq.), b) converting a compound of the formula (VII) into the oxime thereof, the oxime ether or ester thereof, and reducing the latter, for example, with NaBH$_4$, NaBH$_3$CN, LiAlH$_4$ or diborane (compare J. Org. Chem. 34 (1969), 1817).

When, in process 4 b, 1-(2-methoxy-5-pyridyl)-2-formylamino-2-methylpropane is used as compound of the formula XXII, the process can be depicted by the following formula diagram:

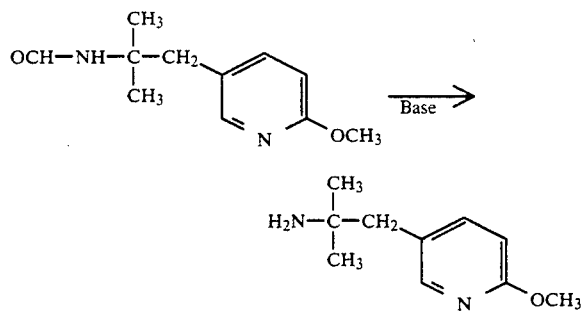

The compounds of the formula XXII are new. Their preparation is described hereinafter in process 24. Compounds of the formula XXII which are preferably used are those in which R$^4$ has the preferred and particularly preferred meanings specified hereinbefore for the compounds of the formula I, and R$^{11}$ represents the radicals —NHCHO and —NHCOCH$_3$. The following specific compounds of the formula XXII may be mentioned:

1-[2-(2-methoxyethoxy)-5-pyridyl]-2-formylamino-2-methylpropane

1-[2-(2-ethoxyethoxy)-5-pyridyl]-2-formylamino-2-methylpropane

1-[2-(2-ethoxyethoxy)-5-pyridyl]-2-acetamino-2-methylpropane.

Process 4 b is carried out by reacting compounds of the formula XXII preferably in the presence of water-soluble organic diluents and inorganic bases.

Bases which may be mentioned are alkali metal and alkaline earth metal hydroxides, carbonates, bicarbonates.

The bases are used in equimolar quantity or in an up to 20-fold, preferably 3- to 10-fold, excess relative to the compounds of the formula XXII.

Diluents which are preferably used are water-miscible organic solvents such as alcohols, for example methanol, ethanol, dioxane, ethylene glycol dimethyl ether, diethylene glycol dimethyl ether, dimethylformamide, dimethyl sulphoxide, sulpholane, N-methylpyrrolidone. Temperatures from 20° to 200° C., preferably 50° to 180° C., are used.

When, in process 6), the 2-[3-[5-(2-methoxyethoxy)-2-pyridyl]]propylamide of (2-fluorophenyl)acetoxyacetic acid is used as compound of the formula (X), the process can be depicted by the following reaction scheme:

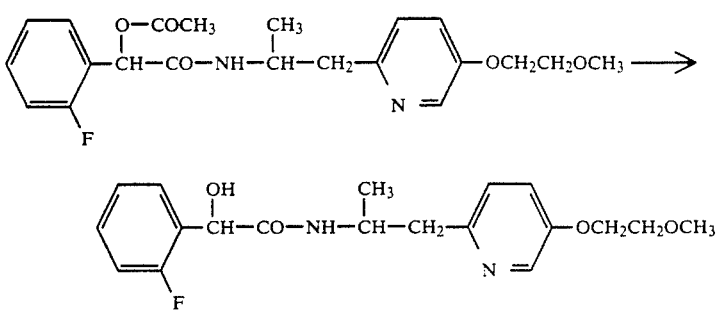

Compounds of the formula (X) are new. Their preparation is described hereinafter. The substituents R$^0$ to R$^4$ and A preferably have the meanings specified hereinbefore as preferred for the compounds of the formula (I). The following specific compounds of the formula (X) may be mentioned:

2-[3-[5-(2-Methoxyethoxy)]-2-pyridyl-propylamide of (3-chlorophenyl)acetoxyacetic acid, 2-[3-[5-(2-Ethoxyethoxy)]-2-pyridyl)propylamide of (2-fluorophenyl)acetoxyacetic acid, 2-[3-[5-(2-Methoxyethoxy)]-2-pyridyl]propylamide of (6-chloro-2-pyridyl)acetoxyacetic acid, 2-[3-[5-(2-Ethoxyethoxy)]-2-pyridyl]propylamide of (4,6-dichloro-2-pyridyl)acetoxyacetic acid, 2-[3-[5-(2-Methoxyethoxy)]-2-pyridyl]propylamide of (2,6-dichloro-4-pyridyl)acetoxyacetic acid, 2-[3-[2-(2-Methoxyethoxy)]-5-pyridyl]propylamide of (3-chlorophenyl)acetoxyacetic acid, 2-[3-[2-(2-Ethoxyethoxy)]-5-pyridyl]propylamide of (6-chloro-2-pyridyl)acetoxyacetic acid.

Inorganic acids or bases are used to eliminate the acetyl group. These include hydrohalic acids such as hydrochloric acid, sulphuric acid, phosphoric acid, or bases such as sodium hydroxide, potassium hydroxide.

The process is carried out by treating the compound (X) in a diluent as solubilizer with excess aqueous solution of the inorganic acid or base.

The reaction is carried out at temperatures from 20° C. to +150° C.

It is preferably carried out under atmospheric pressure.

It is possible to use as diluents all inert organic solvents which are miscible with water. These include ethers such as tetrahydrofuran, dioxane, nitriles such as acetonitrile, amides such as dimethylformamide, alcohols such as methanol, ethanol, dimethyl sulphoxide.

When, in process 8), 2-fluorobenzaldehyde is used as compound of the formula (XI), and 3-(5-methoxy-2-pyridyl)-2-propyl isonitrile is used as isonitrile of the formula (XII), process 8) can be depicted by the following formula diagram:

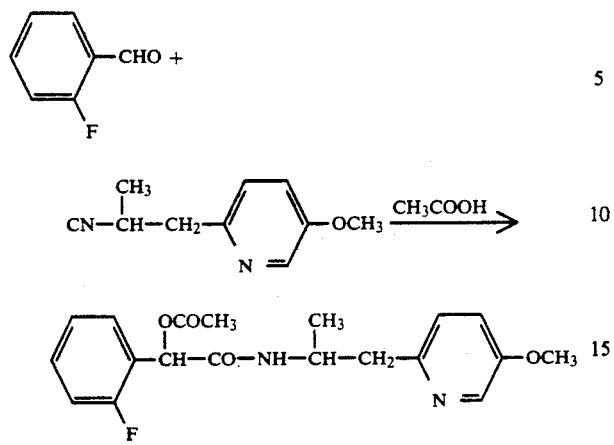

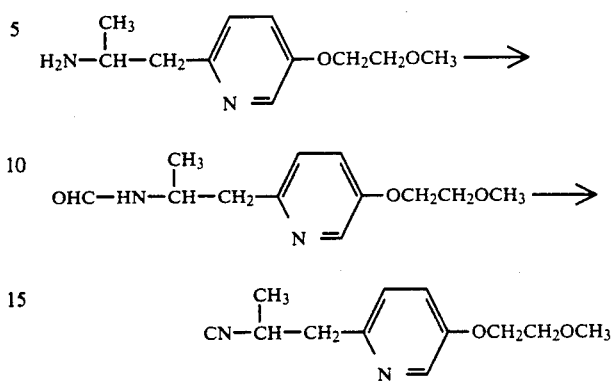

Compounds of the formula (XI) are known (compare, for example, DE-OS (German Published Specification) 3,615,293, U.S. Pat. No. 4,522,822, EP 23,385). The substituents $R^1$ to $R^3$ and A preferably have the meanings specified hereinbefore as preferred for the compounds of the formula (I). The following specific compounds of the formula (XI) may be mentioned:

2-Chloropyridine-4-aldehyde,
2-Cyanopyridine-4-aldehyde,
2,6-Dichloropyridine-4-aldehyde,
2-Aminopyridine-5-aldehyde,
2-Amino-3-chloropyridine-5-aldehyde,
2-Amino-3-cyanopyridine-5-aldehyde,
2-Chloro-3-aminopyridine-6-aldehyde,
2-Cyano-3-aminopyridine-6-aldehyde,
2,4-Dichloro-3-aminopyridine-6-aldehyde,
3-Amino-4-cyanopyridine-6-aldehyde,
2-Chloropyridine-6-aldehyde,
2,4-Dichloropyridine-6-aldehyde,
3-Chlorobenzaldehyde,
4-Amino-3,5-dichlorobenzaldehyde,
4-Amino-3cyanobenzaldehyde.

Isonitriles of the formula (XII) are new. Their preparation is described hereinafter (process 10). The substituents $R^0$ and $R^4$ preferably have the meanings specified hereinbefore as preferred for the compounds of the formula (I). The following specific compounds of the formula (XII) may be mentioned:

3-[2-(2-Methoxyethoxy)-5-pyridyl]-2-propylisonitrile,
3-[2-(2-Ethoxyethoxy)-5-pyridyl]-2-propylisonitrile,
3-[5-(2-Methoxyethoxy)-2-pyridyl]-2-propylisonitrile,
3-[5-(2-Ethoxyethoxy)-2-pyridyl]-2-propylisonitrile.

The process is carried out by reacting the compound (XI) with twice the molar amount of the isonitrile of the formula (XII) and acetic acid in a diluent.

The reaction is carried out at temperatures from 0° C. to +150° C.

It is preferably carried out under atmospheric pressure.

All inert organic solvents are used as diluents. These include, in particular, optionally halogenated aliphatic and aromatic hydrocarbons such as pentane, hexane, cyclohexane, benzene, toluene, methylene chloride, chloroform, chlorobenzene, ethers such as diethyl ether, tetrahydrofuran, nitriles such as acetonitrile and benzonitrile.

When, in process 10), 1-[5-(2-methoxyethoxy)-2pyridyl]-2-aminopropane is used as compound of the formula (III), the process can be depicted by the following formula diagram:

The preparation of the new compounds of the formula III has already been described above.

The reaction is carried out in a manner known per se, for example by initially converting an amine of the formula III into the corresponding N-formyl compound and subsequently reacting the latter, for example with phosgene, to give the isonitrile (compare in this connection: J. Ugi et al., Angew. Chem. 77 (1965), 492).

When, in process 12a), 5-(2-methoxyethoxy)-2-methylpyridine is used as compound of the formula (XIV), the process can be depicted by the following reaction scheme:

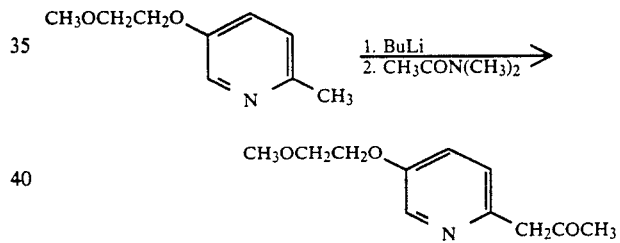

Some of the compounds of the formula (XIV) are new. The preparation of the new compounds is described hereinafter. The substituents $R^{10}$ and Z preferably have the meanings specified hereinbefore as preferred. The following specific compounds of the formula (XIV) may be mentioned:

5-Methoxy-2-methylpyridine,
5-Ethoxy-2-methylpyridine,
5-(2-Ethoxyethoxy)-2-methylpyridine.

Process 12a) is carried out by lithiating a compound of the formula (XIV) in a diluent using an organolithium compound and subsequently reacting with N,N-dimethylacetamide. The following diluents are used: saturated and unsaturated aliphatic and aromatic hydrocarbons such as pentane, hexane, heptane, benzene, ethers such as diethyl ether and tetrahydrofuran.

n-Butyllithium is preferably used as organolithium compound.

The reaction is carried out at temperatures from −100° C. to +50° C. and under atmospheric pressure.

When, in process 12b), 2-nitro-1-[2-(2-methoxyethoxy)-5-pyridyl]-1-propene is used as compound of the formula (XV), the process can be depicted by the following formula diagram:

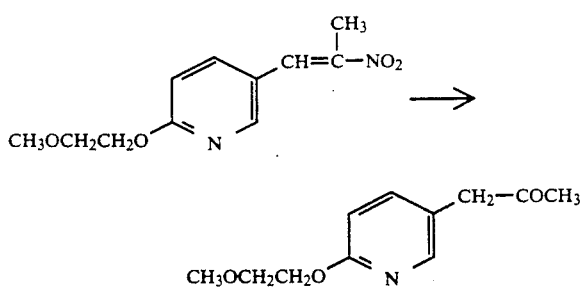

Compounds of the formula (XV) are new. Their preparation is described hereinafter. The substituents $R^{10}$ and Z preferably have the meanings specified hereinbefore as preferred. The following specific compounds of the formula (XV) may be mentioned:
2-Nitro-1-[2-(2-ethoxyethoxy)-5-pyridyl]-1-propene
2-Nitro-1-(2-methoxy-5-pyridyl)-1-propene
2-Nitro-1-(2-ethoxy-5-pyridyl)-1-propene.

The process is carried out by reducing a compound of the formula (XV) in the presence of an inor9anic or organic acid, with the oxime which is formed as an intermediate being directly hydrolyzed to the ketone.

The compound of the formula (XV) can also be reduced with hydrogen in the presence of a catalyst and subsequently hydrolized.

Iron/hydrochloric acid and zinc/glacial acetic acid are used as reducing agents.

The catalytic reduction is preferably carried out with palladium/charcoal in pyridine, and this is followed by hydrolysis with dilute mineral acids such as sulphuric acid or hydrochloric acid.

The reaction is carried out at temperatures from room temperature to the boiling point of the solvent used.

It is carried out under atmospheric pressure or under elevated pressure.

When, in process 14), 2-methoxyethyl p-toluenesulphonate is used as compound of the formula (XII), the process can be depicted by the following formula diagram:

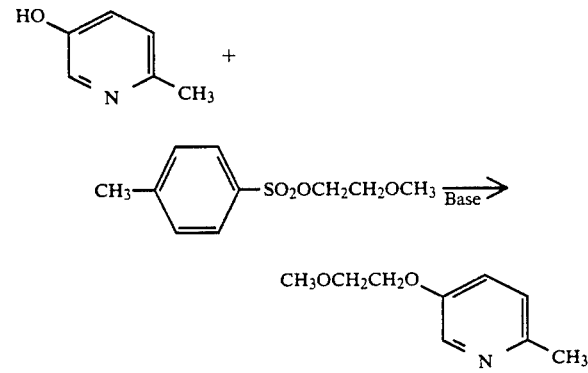

Compounds of the formula (XVII) are known. The following specific compounds of the formula (XVII) may be mentioned:
2-Methoxyethyl methanesulphonate
2-Ethoxyethyl methanesulphonate
2-Ethoxyethyl p-toluenesulphonate The process is carried out by reacting equimolar amounts of 5-hydroxy-2-methylpyridine and compound (XVII) in the presence of equimolar amount of a base in a diluent.

Alcohols such as methanol or ethanol are preferably used as diluents.

The corresponding alkali metal alcoholates suc as sodium methylate and ethylate are used as bases.

The reaction is carried out at room temperature up to the boiling point of the solvent used. It is preferably carried out under atmospheric pressure.

When, in process 16), 2-ethoxypyridine-5-aldehyde is used as compound of the formula (XVIII), the process can be depicted by the following formula diagram:

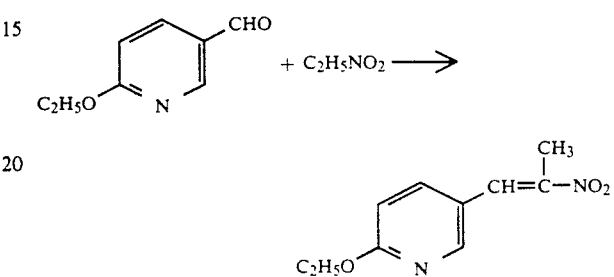

Some of the aldehydes of the formula (XVIII) are new. The preparation of the new compounds of the formula (XVIII) is described hereinafter (processes 18 a and b). The substitents $R^{10}$ and Z preferably have the meanings specified hereinbefore as preferred. The following specific compounds of the formula (XVIII) may be mentioned:
2-(2-Methoxyethoxy)pyridine-5-aldehyde
2-(2-Ethoxyethoxy)pyridine-5-aldehyde The process is carried out by condensing equivalent amounts of the compound (XVIII) and nitroethane in a diluent with the addition of a base.

The reaction is carried out at temperatures from 0° C. to +150° C.

It is preferably carried out under atmospheric pressure.

Aromatic hydrocarbons such as benzene, toluene, xylene, alcohols such as methanol, ethanol, organic carboxylic acids such as acetic acid are used as diluents.

The following are used as bases: primary amines such as methylamine, ethylamine, combinations of hydrochlorides of primary amines such as methylamine hydrochloride, ethylamine hydrochloride with sodium carbonate, secondary amines such as piperidine, tertiary amines such as triethylamine, ammonium salts of organic carboxylic acids such as ammonium acetate.

When, in process 18 a, 2-ethoxy-5-pyridylmethanol is used as compound of the formula (XIX), the process can be represented by the following formula diagram:

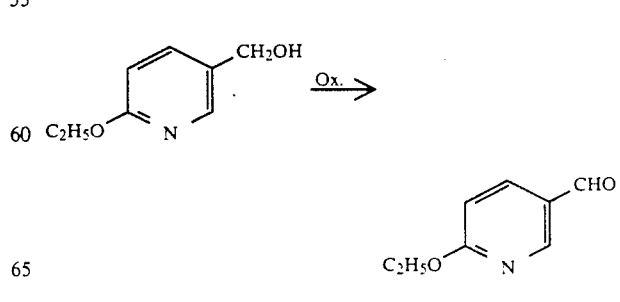

Some of the compounds of the formula (XIX) are new. The preparation of the new compounds of the formula (XIX) is described hereinafter (process 20). The substituents $R^{10}$ and Z preferably have the meanings specified hereinbefore as preferred. The following specific compounds of the formula (XIV) may be mentioned:

2-(2-Methoxyethoxy)-5-pyridylmethanol
2-(2-Ethoxyethoxy)-5-pyridylmethanol

The following may be mentioned as oxidizing agents for carrying out process 18a): a) activated DMSO such as DMSO/acetic anhydride, DMSO/thionyl chloride, DMSO/oxalyl chloride, and b) manganese dioxide.

Process 18aa) is carried out by reacting the alcohol of the formula (XIX) with 1-1.5 equivalents of the oxidizing agent.

The reaction is carried out at temperatures from $-70°$ C. to $+25°$ C.

It is preferably carried out under atmospheric pressure.

Inert organic solvents are used as diluents. The following may be mentioned as examples:

Optionally chlorinated hydrocarbons such as methylene chloride, chloroform, ethers such as diethyl Process 18ab) is carried out by reacting the alcohol of the formula (XIX) with excess manganese dioxide.

The reaction is carried out at temperatures from 20° C. to $+150°$ C. It is preferably carried out under atmospheric pressure.

The following are used as diluents: inert organic solvents, especially aliphatic and aromatic, optionally halogenated hydrocarbons such as pentane, hexane, cyclohexane, benzene, toluene, methylene chloride, chloroform, ethers such as diethyl ether and tetrahydrofuran.

Process 18b for the preparation of the compounds of the formula XVIII is carried out in analogy to the process described by A. S. Dainter et. al., Tetrahedron Letters 25 (1984), pages 5693-5696.

When, in process 20 6-ethoxynicotinic acid is used as compound of the formula (XX), the process can be depicted by the following formula diagram:

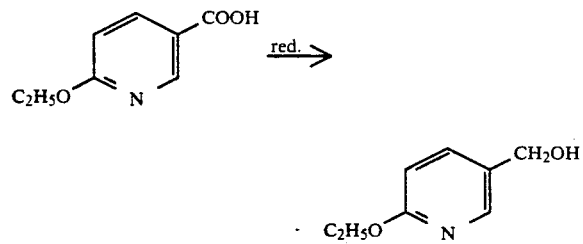

Some of the compounds of the formula (XX) are known. The preparation of the new compounds of the formula (XX) is described hereinafter (process 22). The substituents $R^{10}$ and Z preferably have the meanings specified hereinbefore as preferred. The following specific compounds of the formula (XX) may be mentioned:

6-Methoxynicotinic acid,
6-(2-Methoxyethoxy)nicotinic acid,
6-(2-Ethoxyethoxy)nicotonic acid.

Boranes such as, for example, diborane, complex metal hydrides such as, for example, $LiAlH_4$ are used as reducing agents.

The process is carried out by reacting the compound of the formula (XX) in a diluent with the 1-4 molar amount of reducing agent.

The reaction is carried out at temperatures from $-50°$ C. to $+100°$ C., and is preferably carried out under atmospheric pressure.

Ethers such as diethyl ether, tetrahydrofuran, dioxane are used as diluents.

When, in process 22), 2-ethoxyethanol is used as compound of the formula (XXI), the process can be represented by the following formula diagram:

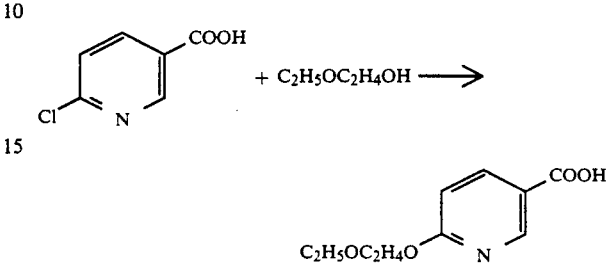

Compounds of the formula (XXI) are known. The substituents $R^{10}$ and Z preferably have the meanings specified hereinbefore as preferred. The following specific compounds of the formula (XXI) may be mentioned: methanol, ethanol, 2-methoxyethanol, 2-ethoxyethanol.

The process is carried out by reacting 6-chloronicotinic acid with 1-5 times, preferably 1.5-2 times, the molar amount of the compound of the formula (XXI) in the presence of 2-10 times, preferably 4-7 times, the molar amount of a base and 5-25, preferably 10-15, molepercent of a quaternary ammonium salt in a diluent. Alkali metal and alkaline earth metal hydroxides such as, for example, sodium hydroxide, potassium hydroxide, alkali and alkaline earth metal carbonates such as sodium carbonate, potassium carbonate, are used as bases. Tetraalkylammonium halides, for example tetrabutylammonium bromide, are preferably used as quaternary ammonium salts.

The following are used as diluents: saturated and unsaturated aliphatic and aromatic hydrocarbons such as pentane, hexane, heptane, cyclohexane, benzene, toluene, ethers such as tetrahydrofuran, dioxane and dimethyl formamide and dimethyl sulphoxide.

The reaction is carried out at temperatures from $+20°$ C. to $+180°$ C., preferably at the boiling point of the diluent used.

It is preferably carried out under atmospheric pressure.

When, in process 24, 1-(2-ethoxy-5-pyridyl)-2-methyl-1-propene is used as compound of the formula XXIII, the process can be depicted by the following reaction scheme:

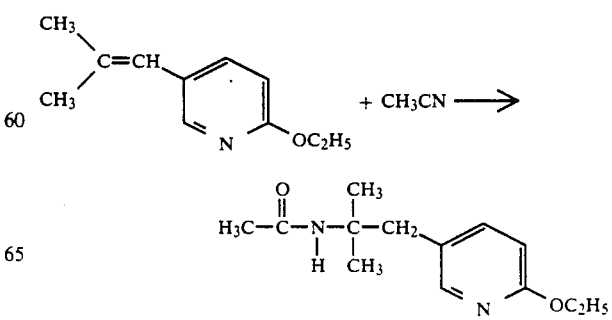

The compounds of the formula XXIII are new. The preparation is described hereinafter (process 26). The substituent $R^4$ in formula XXIII preferably has the meanings specified for the compounds of the formula I. The following specific compounds of the formula (XXIII) may be mentioned:

1-[2-(2-Methoxyethoxy)-5-pyridyl]-2-methyl-1-propene
1-[2-(2-Ethoxyethoxy)-5-pyridyl]-2-methyl-1-propene.

Organic nitriles which may be mentioned as preferred for carrying out the reaction are: acetonitrile, propionitrile, benzonitrile. The reaction can also be carried out with alkali metal or alkaline earth metal cyanides and with hydrocyanic acid.

The reaction is carried out in the presence of acids. Those which may be mentioned as preferred are: sulphuric acid, perchloric acid, phosphoric acid, polyphosphoric acid, alkylsulphonic acids such as methanesulphonic acid, trifluoromethanesulphonic acid.

The reaction is carried out at temperatures from $-20°$ to $+70°$ C., preferably from $-10°$ to $+50°$ C.

1 to 2 equivalents of the nitriles or cyanides and 1 to 5 equivalents of acid are used per mole of compound of the formula XXIII. The reaction can also be carried out in an excess of the acid, which then acts as diluent.

The reaction can be carried out in all organic diluents which are inert under the reaction conditions. These include, in particular, aliphatic, aromatic, optionally substituted hydrocarbons such as pentane, hexane, heptane, cyclohexane, petroleum ether, petroleum spirit, ligroin, benzene, toluene, methylene chloride, ethylene chloride, chloroform, carbon tetrachloride, chlorobenzene, o-dichlorobenzene, ethers such as diethyl or dibutyl ether, dioxane, acetic acid, propionic acid.

After the end of the reaction, the mixture is diluted with water, neutralized, filtered to remove solid products and, where appropriate, extracted with immiscible solvents.

When, in process 26 a), 2-methoxymethoxy-5-(1-hydroxy-2-methylpropyl)pyridine is used as compound of the formula XXIV, the process can be depicted by the following formula diagram:

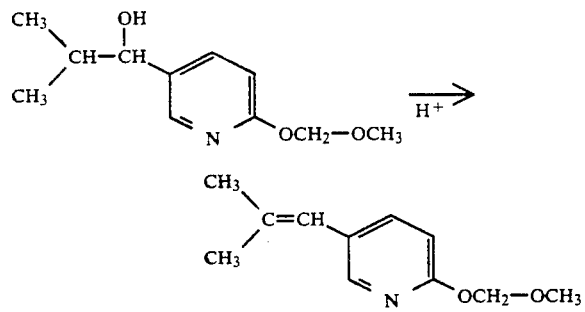

The compounds of the formula XXIV are new. Their preparation is described hereinafter (process 18). $R^4$ has the meanings specified in formula XXIV, preferably the meanings specified for the compounds of the formula I. The following specific compounds of the formula XXIV may be mentioned:

2-(2-Methoxyethoxy)-5-(1-hydroxy-2-methylpropyl)-pyridine
2-(2-Ethoxyethoxy)-5-(1-hydroxy-2-methylpropyl)pyridine The reaction is carried out in the presence of up to 30% by volume (based on the compound of the formula XXIV) of a protonic acid. It is also possible, where appropriate, to dispense with addition of the acid. Suitable acids are: hydrohalic acids such as, for example, hydrochloric acid, sulphuric acid, phosphoric acids, aliphatic and aromatic sulphonic acids such as, for example, methanesulphnic acid, p-toluenesulphonic acid as well as acid ion exchanger resins.

The reaction is carried out at 50° to 250° C., preferably at 50° to 180° C. and under atmospheric pressure.

It is possible, where appropriate, to work in the presence of solvents which are inert under the reaction conditions. Those which may be mentioned are: aliphatic and aromatic hydrocarbons such as pentane, hexane, heptane, cyclohexane, petroleum ether, petroleum spirit, ligroin, benzene, toluene, methylene chloride, ethylene chloride, chloroform, carbon tetrachloride, chlorobenzene and o-dichlorobenzene, as well as ethers such as diethyl and dibutyl ether, glycol, dimethyl ether and diglycol dimethyl ether, tetrahydrofuran and dioxane, additionally esters such as methyl and ethyl acetate, as well as nitriles such as, for example, acetonitrile and propionitrile, benzonitrile, furthermore amides such as, for example, dimethylformamide, dimethylacetamide and N-methylpyrrolidone, as well as tetramethylene sulphone and hexamethylphosphoric triamide.

After the reaction is complete, the reaction mixture is neutralized, solvent is removed by distillation, and the product is isolated.

Process 26 b is carried out in 2 stages and can be described by the following reaction scheme. Initially, the compound of the formula XXIV is converted by reaction with a halogenating agent into the corresponding halide, and the latter is subsequently reacted in the presence of a base to give the vinyl-substituted pyridine.

Halogenating agents which may be mentioned are: sulphonyl chloride, phosgene, phosphorus oxychlorides, $PCl_3$, $PCl_5$ as well as the corresponding bromides. It is also possible to use in place of a halogenating agent a sulphonylating agent such as methanesulphonyl chloride.

The halogenation or sulphonylation is carried out at $-20°$ to $+150°$ C., preferably at 0° to 80° C. and under atmospheric pressure.

1 to 2 equivalents of halogenating agent or sulphonylating agent are used per mole of compound of the formula XXIV.

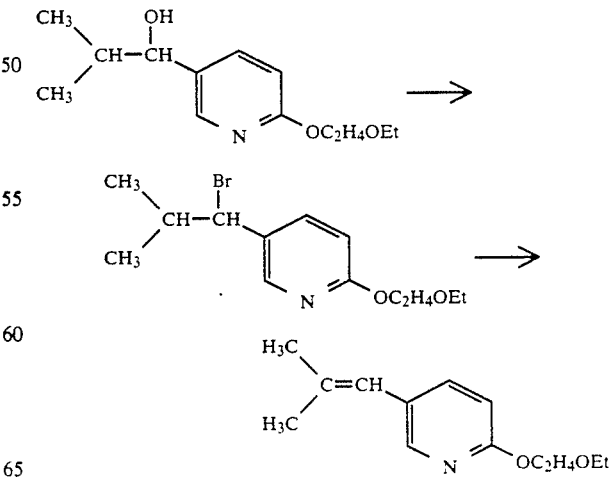

The halogenating agent can be used in excess as diluent. Other diluents are: aliphatic and aromatic hydrocarbons such as pentane, hexane, heptane, cyclohexane, petroleum ether, petroleum spirit, ligroin, benzene, toluene, methylene chloride, ethylene chloride, chloroform, carbon tetrachloride, chlorobenzene and o-dichlorobenzene, as well as ethers such as diethyl and dibutyl ether, glyol dimethyl ether and diglycol dimethyl ether, tetrahydrofuran and dioxane, additionally esters such as methyl and ethyl acetate, as well as nitriles such as, for example, acetonitrile and propionitrile, benzonitrile, furthermore amides such as, for example, dimethylformamide, dimethylacetamide and N-methylpyrrolidone, as well as tetramethylene sulphone and hexamethylphosphoric triamide.

The working up is carried out in a customary manner after the reaction mixture has been neutralized.

The following may be mentioned for the elimination reaction to give the olefin: alkali metal alcoholates such as sodium methylate, potassium, tert.-butylate, alkali metal amides such as sodiumamide, lithium diisopropylamide, tertiary amines such as ethyl diisopropylamine, diazabicycloundecene, diazabicyclononene, alkali metal hydroxides such as NaOH and KOH.

The elimination is carried out at 20° to 200° C., preferably at 50° to 150° C., and under atmospheric pressure.

1 to 1.5 equivalents of base per mole are used. Liquid bases can also be used as solvent. Other suitable diluents are virtually all inert organic solvents. These include, in particular, aliphatic and aromatic, optionally halogenated hydrocarbons such as pentane, hexane, heptane, cyclohexane, petroleum ether, petroleum spirit, ligroin, benzene, toluene, methylene chloride, ethylene chloride, chloroform, carbon tetrachloride, chlorobenzene and o-dichlorobenzene, as well as ethers such as diethyl and dibutyl ether, glycol dimethyl ether and diglycol dimethyl ether, tetrahydrofuran and dioxane, additonally esters such as methyl and ethyl acetate, as well as nitriles such as, for example, acetonitrile and propionitrile, benzonitrile, glutarodinitrile, furthermore amides such as, for example, dimethylformamide, dimethylacetamide and N-methylpyrrolidone, as well as tetramethylene sulphone and hexamethylphosphoric triamide. When, in proces 28, 2-(2-ethoxyethoxy)-pyridine-5-carbaldehyde is used as compound of the formula XVIII, the process can be depicted by the following reaction scheme:

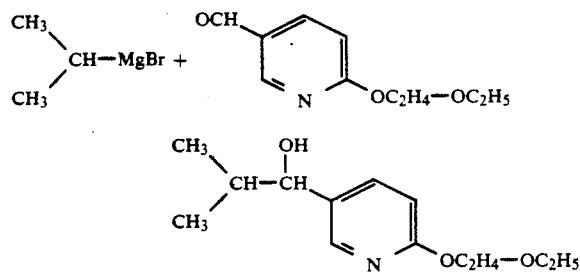

The compounds of the formula XVIII are new. The preparation is described under process 18. The compounds of the formula XVIII mentioned for process 16 are preferably used.

The Grignard compounds of the formula XXV are known. 1 to 2 moles of Grignard compound of the formula XXV areused per mole of compound of the formula XVIII.

Temperatures from −20° to 100° C., preferably from 0° to 80° C., are used.

Preferred diluents which may be mentioned are: aliphatic and aromatic hydrocarbons such as pentane, hexane, heptane, cyclohexane, petroleum ether, petroleum spirit, ligroin, benzene, toluene, chlorobenzene and o-dichlorobenzene, as well as ethers such as diethyl and dibutyl ether, glycol dimethyl ether and diglycol dimethyl ether, tetrahydrofuran and dioxane, as well as hexamethylphosphoric triamide.

The working up is carried out after the reaction is complete by hydrolysis, neutralization and extraction.

The active compounds are used as production promoters in livestock to promote and accelerate growth and the production of milk and wool, and to improve the feed conversion and the meat quality, and to displace the meat/fat ratio in favor of meat. The active compounds are used for productive, breeding and ornamental livestock and pets. They are also used to reduce the fatness of overweight livestock and as an agent for treating obesity in humans and animals.

The productive and breeding livestock include mammals such as, for example, cattle, pigs, horses, sheep, goats, rabbits, hares, deer, fur-bearing livestock such as mink, chinchilla, poultry such as, for example, chickens, geese, ducks, turkeys, pigeons, fish such as, for example, carp, trout, salmon, eels, tench, pike, reptiles such as, for example, snakes and crocodiles.

The ornamental livestock and pets include mammals such as dogs and cats, birds such as parrots, canaries, fish such as ornamental and aquarium fish, for example goldfish.

The active compounds are used, irrespective of the sex of the livestock, during all phases of growth and production of the livestock.

The active compounds are preferably used during the intensive phase of growth and production. The intensive phase of growth and production lasts from one month up to 10 years depending on the species.

The amount of the active compounds which are administered to the livestock to achieve the desired effect can be varied substantially because of the beneficial properties of the active compounds. It is preferably about 0.001 to 50 mg/kg, in particular 0.01 to 5 mg/kg, of body weight per day. The appropriate amount of the active compound and the appropriate duration of administration depend, in particular, on the species, the age, the sex, the state of health and the type of housing and feeding of the livestock and can easily be determined by all those skilled in the art.

The active compounds are administered to the livestock by the customary methods. The mode of administration depends, in particular, on the species, the behavior and the state of health of the livestock.

The administration is carried out orally or parenterally in formulations suitable for this purpose or in pure form. Oral formulations are powders, tablets, granules, doenches, boli and feedstuffs, premixes for feedstuffs, formulations for administration via the drinking water.

The oral formulations contain the active compound in concentrations of 0.01 ppm-100%, preferably of 0.01 ppm-1%.

The active compounds can be administered once. However, the active compounds can also be administered temporarily or continuously during the whole or during a part of the phase of growth and production.

In the case of continuous administration, usage can take place once or several times a day at regular or irregular intervals.

The active compounds can be present in the formulations alone or mixed with other production-promoting element compounds, vitamins, nitrogen-providing nonprotein compounds, coloring agents, antioxidants, flavorings, emulsifiers, flow regulators, preservatives and pelletinq aids.

Other production-promoting active compounds are: for example antibiotics such as tylosin and virginamycin. Mineral feedstuffs are, for example, dicalcium phosphate, magnesium oxide, sodium chloride. Trace element compounds are, for example, iron fumarate, sodium iodide, cobalt chloride, copper sulphate, zinc oxide. Vitamins are, for example, vitamin A, vitamin $D_3$, vitamin E, B vitamins, vitamin C.

Nitrogen-providing non-protein compounds are, for example, biuret, urea.

Coloring agents are, for example, carotenoids such as citrana xanthin, zeaxanthin, capsanthin.

Antioxidants are, for example, ethoxyquin, butylhydroxy-toluene.

Flavoring are, for example, vanillin.

Emulsifiers are, for example, esters of lactic acid, lecithin.

Flow regulators are, for example, sodium stearate, calcium stearate.

Preservatives are, for example, citric acid, propionic acid.

Pelleting aids are, for example, lignin sulphonates, cellulose ethers.

The active compounds can also be administered together with the feed and/or the drinking water.

The feed includes single feedstuffs of plant feedstuffs of animal origin such as meat, fats, milk products, bonemeal, fish products, the single feedstuffs such as vitamins, proteins, amino acids, for example DL-methionine, salts such as lime and sodium chloride. The feed also includes supplementary, prepared and compound feedstuffs. These contain single feedstuffs in a composition which ensures a balanced diet in terms of the supply of energy and of protein as well as the supply of vitamins, mineral salts and trace elements.

The concentration of the active compounds in the feed is normally about 0.01-500 ppm, preferably 0.1-50 ppm.

The active compounds can be added to the feed as such or in the form of premixes or feed concentrates.

Example of the composition of a chick rearing feed which contains 10 ppm active compound according to the invention:

200 g of wheat, 340 g of corn, 361 g of soy meal, 60 g of beef tallow, 15 g of dicalcium phosphate, 10 g of calcium carbonate, 4 g of iodized sodium chloride, 7.5 g of vitamin/mineral mix and 2.5 g of the active compound premix specified below provide, after careful mixing, 1 kg of feed with a content of 10 ppm active compound.

1 kg of vitamin/mineral contains: 600 I.U. of vitamin A, 100 I.U. of vitamin D:, 10 mg of vitamin E, 1 mg of vitamin $K_3$, 3 mg of riboflavin, 2 mg of pyridoxine, 20 mcg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$.

2.5 g of active compound premix contain, for example, 10 mg of active compound, 1 g of DL-methionine, remainder soy bean meal.

Example for the composition of a pig rearing feed which contains 8 ppm active compound according to the invention: 630 g of coarse feed cereal meal (composed of 200 g of corn, 150 g of coarse barley meal, 150 g of coarse oatmeal and 130 g of coarse wheatmeal), 80 g of fishmeal, 60 g of coarse soy meal, 60 g of tapioca meal, 38 g of brewer's yeast, 50 g of vitamin/mineral mix for pigs, 30 g of linseed cake meal, 30 g of corn gluten feed, 10 g of soy oil, 10 g of sugar-cane molasses and 2 g of active compound premix (composition, for example, as for chicken feed) provide, after careful mixing, 1 kg of feed with a content of 8 ppm active compound.

The specified feed mixes are designed for rearing and fattening preferably chicks and pigs respectively, but they can also be used in the same or similar composition for feeding other livestock.

EXAMPLE A

Rat feeding trial

Female laboratory rats weighing 90-110 g of the SPF Wistar type (bred by Hagemann) are fed ad lib with standard rat feed to which the desired amount of active compound is added. Each trial series is carried out with feed from the same batch so that differences in the composition of the feed are not able to impair the comparability of the results.

The rats receive water ad lib.

12 rats form a trial group in each case and are fed with feed to which the desired amount of active compound is added. A control group receives feed without active compound. The average body weight and the variation in the body weights of the rats is the same in each trial group so that comparability of the trial groups with one another is ensured.

During the 13-day trial, the weight gain and feed consumption are determined, and the relevant weight gain by comparison with the untreated control is calculated.

The results shown in the table are obtained:

TABLE 1

| Active compound Example No. | Rat feeding trial | | |
|---|---|---|---|
| | Active compound used ppm | Relative weight gain % | Relative fat reduction % |
| 4 | 25 | 25 | 20 |
| 7 | 25 | 13 | 15 |
| 8 | 25 | 44 | 25 |
| 9 | 25 | 30 | 20 |
| 12 | 25 | 10 | 17 |
| | 25 | | |

EXAMPLES

General procedure for process 2a Preparation of compounds of the formula I by process 2a 10 mmol of the compound of the formula II are added in portions, at 0° C., to a solution of 20 mmol of the amine of the formula III in 15 ml of absolute ethanol. The mixture is allowed to reach 10° -15° C. and is then stirred at this temperature for one hour. It is then cooled again to 0° C. and 120 mg (10 mmol) of sodium borohydride are added in portions. The mixture is stirred at room temperature for one hour. Addition of 20 ml of water is followed by stirring for 30 minutes, evaporation and partition between water and ethyl acetate. The organic phase is dried over sodium sulphate and evaporated. The residue is recrystallized or chromatographed.

General procedure for process 2b

Preparation of compounds of the formula I by process 2b 0.1 mol of the compound of the formula IV and 0.11 mol of the amine of the formula III are heated under reflux in 200 ml of methanol overnight. The solvent is stripped off and the residue is recrystallized or chromatographed.

General procedure for process 2c

Preparation of compounds of the formula I by process 2c 10 mmol of the compound of the formula V are dissolved in 150 ml of ethanol, and 20 mmol of the amine of the formula III are added, and the mixture is heated under reflux for 18 hours. The solvent is then stripped off, and the residue is taken up in 100 ml of dry ether. The insoluble amine hydrohalide is filtered off, and the ethereal solution is washed with water, dried over sodium sulphate and evaporated. The crude product is recrystallized or chromatographed.

General procedure for process 2d

Preparation of compounds of the formula I by process 2d 10 mmol of the compound VI and 10 mmol of the compound VII are heated under reflux in 40 ml of dry ethanol with the addition of 4 g of 4 Å molecular sieves for 30 minutes. The mixture is cooled to 0° C. and then 12 mmol of NaBH₄ are added, followed by stirring at 0° C. for one hour. The pH is then adjusted to 3 with dilute hydrochloric acid, the ethanol is stripped off, the residue is taken up in water, and the solution is washed with ether. The aqueous phase is made alkaline with dilute sodium hydroxide solution and extracted with chloroform. Drying over sodium sulphate is followed by evaporation.

General procedure for process 2e

Preparation of compounds of the formula I by process 2e 15 mmol of the amine of the formula III are added dropwise to a solution of 10 mmol of the compound of the formula VIII in 50 ml of ethanol at 10° -15° C. The mixture is allowed to reach room temperature and is then stirred for 15 minutes. It is then diluted with a further 100 ml of ethanol and, at 0° -5° C., 80 mmol of sodium borohydride are added in portions. The mixture is allowed to reach room temperature and is stirred for one hour. Then 200 ml of water are added at 10° C., the mixture is stirred for 30 min, the ethanol is evaporated off, and the residue is extracted three times with 50 ml of dichloromethane each time. The combined organic phases are washed with 100 ml of water, dried over sodium sulphate and evaporated.

General procedure for process 2f

Preparation of compounds of the formula I by process 2f 2.3 mmol of the compound IX in 30 ml of absolute tetrahydrofuran are added dripwise to 12.4 ml of a 1 M solution of borane in tetrahydrofuran. The mixture is heated udner reflux for 1 hour, diluted with ice-water, and 50 ml of 1N hydrochloric acid are added. The organic solvent is evaporated off and then the acidic aqueous solution is extracted twice with 30 ml of ether each time and then made alkalien with saturated 30 ml carbonate solution and extracted three times with 30 ml ethyl acetate each time. The combined extracts are dried over sodium sulphate and evaporated.

The following compounds are prepared in analogy to processes 2a–2f specified above:

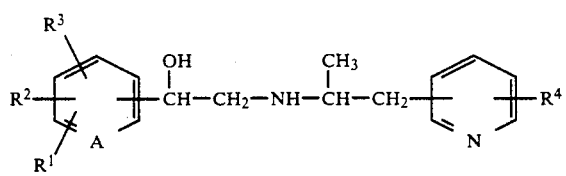

mixtures of diastereomers in each case

| Example No. | R³, R², R¹, A | (pyridyl)-R⁴ | Yield [%] in the process | ¹H-NMR (CDCl₃, δ [ppm]) |
|---|---|---|---|---|
| 1 | Cl, N, Cl (dichloropyridyl) | pyridyl | 60 | 1.1 (dd, 3H); 2.0–3,3 (m, 7H); 4.6 (m, 1H); 7.2 (m, 4H); 7.6 (m, 1H); 8.5 (m, 1H). |

-continued

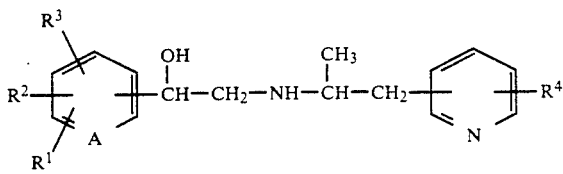

mixtures of diastereomers in each case

| Example No. | R¹, R², R³, A | Pyridine R⁴ | Yield [%] in the process | ¹H-NMR (CDCl₃, δ [ppm]) |
|---|---|---|---|---|
| 2 | 3-Cl-phenyl | 2-pyridyl | 86 | 1.1 (dd, 3H); 1.8–3.3 (m, 7H); 4.6 (m, 1H); 7.2 (m, 6H); 7.6 (m, 1H); 8.5 (m, 1H). |
| 3 | 3-Cl-phenyl | 3-pyridyl | 65 | 1.2 (dd, 3H); 2.2–3.0 (m, 7H); 4.6 (m, 1H); 7.2 (m, 4H); 7.5 (m, 1H); 8.5 (m, 3H). |
| 4 | 2-amino-3-chloro-5-methyl-pyridyl | 3-pyridyl | 61 | 1.2 (dd, 3H); 2.0–3.0 (m, 7H); 4.5 (m, 1H); 4.9 (s, 2H); 7.2 (m, 1H); 7.5 (m, 1H); 7.9 (m, 1H); 8.5 (m, 3H) |
| 5 | 2-amino-3-chloro-5-methyl-pyridyl | 2-pyridyl | 61 | 1.2 (dd, 3H); 2.2–3.1 (m, 6H); 3.4 (m, 1H); 4.6 (m, 1H); 5.0 (s, 2H); 7.1 (m, 2H); 7.6 (m, 2H); 7.9 (m, 1H); 8.5 (m, 1H). |
| 6 | 3-Cl-phenyl | 4-pyridyl | 71 | 1.1 (dd, 3H); 2.2–3.0 (m, 7H); 4.6 (m, 1H); 7.2 (m, 5H); 8.5 (m, 3H). |
| 7 | 2-amino-3-chloro-5-methyl-pyridyl | 4-pyridyl | 73 | 1.1 (dd, 3H); 2.2–3.0 (m, 7H); 4.5 (m, 1H); 4.9 (s, 2H); 7.1 (m, 2H); 7.5 (m, 1H); 7.9 (m, 1H); 8.5 (m, 2H). |
| 8 | 2,6-dichloropyridyl | 6-(OC₂H₄OC₂H₅)-3-pyridyl | 99 | 1.1 (dd, 3H); 1.3 (t, 3H); 1.9–3.1 (m, 7H); 3.6 (q, 2H); 3.8 (t, 2H); 4.4 (t, 2H); 4.6 (m, 1H); 6.8 (m, 1H); 7.2 (m, 2H); 7.4 (m, 1H); 7.9 (m, 1H). |
| 9 | 3-Cl-phenyl | 6-(OC₂H₄OC₂H₅)-3-pyridyl | 97 | 1.1 (dd, 3H); 1.3 (t, 3H); 2.1–3.0 (m, 7H); 3.6 (q, 2H); 3.8 (t, 2H); 4.4 (t, 2H); 4.6 (m, 1H); 6.7 (m, 1H); 7.2–7.4 (m, 5H); 8.0 (m, 1H). |

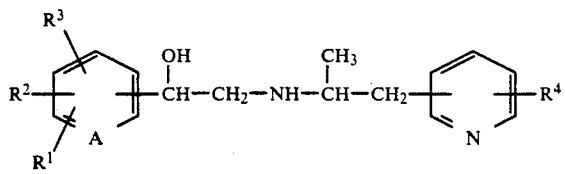

mixtures of diastereomers in each case

| Example No. | R³, R², R¹, A (aryl) | Pyridyl-R⁴ | Yield [%] in the process | ¹H-NMR (CDCl₃, δ [ppm]) |
|---|---|---|---|---|
| 10 | 3-Cl-phenyl | 5-OC₂H₄OC₂H₅-pyridin-2-yl | 80 | 1.1 (dd, 3H); 1.2 (t, 3H); 2.0–3.0 (m, 7H); 3.6 (q, 2H); 3.8 (m, 2H); 4.1 (m, 2H); 4.6 (m, 1H); 7.1–7.4 (m, 6H); 8.3 (m, 1H). |
| 11 | 2,4-di-Cl-phenyl | 5-OC₂H₄OC₂H₅-pyridin-2-yl | 97 | 1.1 (dd, 3H); 1.2 (t, 3H); 1.6–2.9 (m, 6H); 3.1 (m, 1H); 3.6 (q, 2H); 3.8 (t, 2H); 4.4 (t, 2H); 4.6 (m, 1H); 6.7 (m, 1H); 7.2 (m, 1H); 7.4 (m, 2H); 7.9 (m, 1H). |
| 12 | 3-Cl-phenyl | 5-COOC₂H₅-pyridin-2-yl | 64 | 1.1 (dd, 3H); 1.4 (t, 3H); 2.5–3.1 (m, 3H); 4.4 (q, 2H); 4.65 (m, 1H); 7.1–7.4 (m, 5H); 8.2 (m, 1H); 9.1 (m, 1H). |

Example 13

N-[(2-(2-Ethoxy-ethyleneoxy)-5-pyridyl)-1,1-dimethylethyl]-1-(3-chlorophenyl)-2-aminoethanol 0.5 g (2.14 mmol) of ω-bromo-3-chloroacetophenone and 2.1 g (4.62 mmol) of 2-(2-ethoxy-ethyleneoxy)-5-(2-amino-2-methylpropyl)-pyridine are heated under reflux in 6 ml of dry acetonitrile for 15 minutes. The mixture is subsequently evaporated in vacuo, the residue is taken up in 10 ml of dry methanol, cooled to 0° C., and 370 mg (9.8 mmol) of NaBH₄ are introduced in portions. The mixture is subsequently stirred at 0° C. for 30 minutes, then poured onto 200 ml of water and extracted with ether. The extract is dried with Na₂SO₄ and evaporated. Purification is carried out by chromatography on silica gel with ethyl acetate/methanol.

Yield: 620 mg
Melting point: 74° C.

Example 14

650 mg (2.73 mmol) of 2-(2-ethoxy-ethyleneoxy)-5-(2-amino-2-methyl-propyl)pyridine are stirred with 510 mg (2.73 mmol) of 3-chlorophenyl-glyoxal hydrate and 2 g of 3 Å molecular sieve in 20 ml of dry ethanol at room temperature for 4 hours. The mixture is then cooled with ice, and 300 mg (7.94 mmol) of NaBH₄ are added, and the mixture is stirred without cooling for one hour. For working up, the mixture is filtered, the filtrate is evaporated, and 200 ml of water are added to the residue. The mixture is extracted three times with 70 ml of CH₂Cl₂ each time, and the extract is dried with Na₂SO₄ and evaporated.

The residue is purified by chromatography on silica gel with ethyl acetate/methanol.

Yield: 580 mg
Melting point: 74° C.

The following are prepared in analogy to Examples 13 and 14:

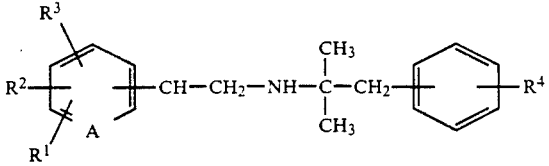
| | | Yield [%] | $^1$H-NMR (CDCl$_3$, δ [ppm]) |
|---|---|---|---|
| 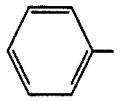 | 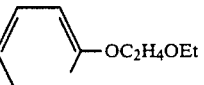 | 27 | 7.9 (d,1H) 7.25-7.4 (m,6H) 6.72 (d,H) 4.65 (dd,1H) 4.45 (t,2H) 3.8 (t,2H) 3.6 (q,2H) 2.97 (dd,1H) 2.7 (dd,1H) 2.61 (s,2H) 1.25 (t,3H) 1.08 (s,6H) |
| 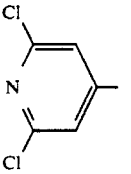 | 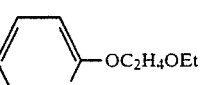 | 26 | 7.9(d,1H), 7.38(dd,1H), 7.3(s,2H), 6.75(d,1H), 4.55(dd,1H), 4.45(t,2H), 3.8(t,2H), 3.6(q,2H), 3.02(dd,1H), 2.6(s,2H), 2.55(dd,1H), 1.25(t,3H), 1.08(s,6H) |
| 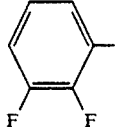 Yield: 65% | 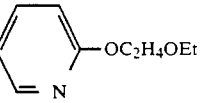 | | 7.9(d,1H), 7.25-7.4(m,2H), 7.0-7.1(m,2H), 6.72(d,1H), 4.95(dd,1H), 4.45(t,2H), 3.8(t,2H), 3.6(q,2H), 3.0(dd,1H), 2.6(s,2H), 2.65(dd,1H), 1.25(t,3H), 1.08(d,6H) |
| 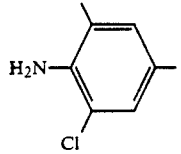 | 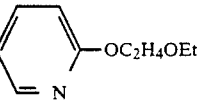 | 57 | 7.9(d,1H, 7.35(dd,1H), 7.2(s,2H), 6.75(d,1H), 4.35-4.5(m,3H), 3.8(t,2H), 3.6(q,2H), 3.9(dd,1H), 2.45-2.65(m,3H), 1.25(t,3H), 1.05(s,6H) Melting Point 75° C. |
| 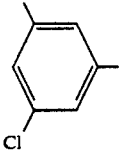 | 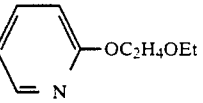 | 25 | Melting Point 66° C. |
| 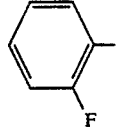 | 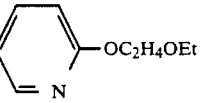 | 40 | Melting Point 58° C. |
| 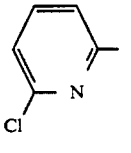 | 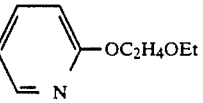 | 17 | 7.(d,1H), 7.67(t,1H), 7.45(d,1H), 7.35(dd,1H), 7.25(d,1H), 6.75(d,1H), 4.2(dd,1H), 4.45(t,2H), 3.28(t,2H), 3.6(q,2H), 3.15(dd,1H), 2.8(dd,1H), 2.5-2.68(m,2H), 1.25(t,3H), 1.07(d,6H) |
| 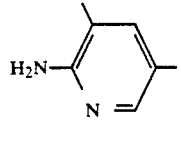 | 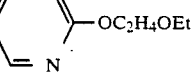 | 34 | Melting Point: 111° C. |

-continued

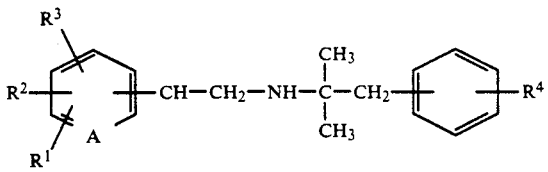

| 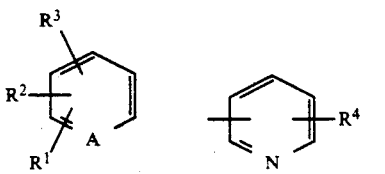 | | Yield [%] | $^1$H-NMR (CDCl$_3$, δ [ppm]) |
|---|---|---|---|
| 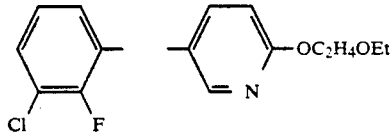 | | 57 | Melting Point: 64° C. |
| 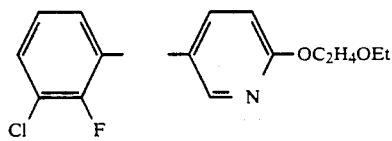 | | 64 | Melting Point: 98° C. |

Example for the preparation of compounds VII by process 4b 2 g (7.5 mmol) of 2-(2-ethoxy-ethyleneoxy)-5-(2-formylamino-2-methylpropyl)-pyridine, 1.92 g (21.6 mmol) of 45% strength NaOH, 20 ml of methanol and 4 ml of water are heated under reflux for 12 hours. After cooling, the mixture is poured onto water and extracted with ether. The extract is dried with Na$_2$SO$_4$ and evaporated. Residue: 1.66 g of yellow oil (93% of theory) $^1$H NMR (CDCl$_3$) 7.95 ppm (d, 1H, H$_{arom}$);
7.42 ppm (dd, 1H, H$_{arom}$);
6.75 ppm (d, 1H, H$_{arom}$);
4.46 ppm (t, 2H, —O—CH$_2$—);
3.8 ppm (t, 2H, Ar—CH$_2$—),
3.1 ppm (q, 2H, —OEt);
2.58 ppm (s, 2H, Ar—CH$_2$—);
1.25 ppm (t, 3H, —OEt);
1.1 ppm (s, 6H, —CH$_3$)

Example for the preparation of the compounds VII and XIII by process 12a)

[5-(2-Ethoxyethoxy)-2-pyridyl]acetone 2.5 ml of a 2.5 M solution of n-butyllithium in hexane are added dropwise at 5° C. to a solution of 1 g (5.5 mmol) of 5-(2-ethoxyethoxy)-2-methylpyridine in 20 ml of tetrahydrofuran. The mixture is stirred at 0°-5° C. for 10 minutes and then 530 mg (6 mmol) of N,N-dimethylacetamide dissolved in a little tetrahydrofuran are added. After stirring at room temperature for 90 minutes, the pH is adjusted to 5 with dilute hydrochloric acid and the tetrahydrofuran is stripped off. The residue is extracted with ethyl acetate, and the organic phase is dried with sodium sulphate and evaporated. Yield: 580 mg (47% of theory), content according to GC/MS: 75%.

Example for the preparation of compounds VII and XIII by process 12b)

[2-(2-Ethoxyethoxy)-5-pyridyl]acetone 6.5 ml of concentrated hydrochloric acid are added dropwise to a boiling suspension of 800 mg (3.2 mmol) of 1-[2-(2-ethoxyethoxy)-5-pyridyl]-2-nitro-1-propene and 710 mg of iron filings in 10 ml of methanol. After 30 minutes the mixture is filtered and diluted with water. It is washed with ether, adjusted to pH 7 and extracted with ether. The organic phase is washed with 1% strength aqueous sodium hydroxide solution and then with water, dried over sodium sulphate and evaporated.
420 mg (60% of theory) of a pale yellow oil are obtained.

$^1$H NMR (CDCl$_3$, δ [ppm]): 1.2 (t, 3H); 2.2 (s, 3H); 3.55 (q, 2H); 3.7 (s, 2H); 3.8 (m, 2H); 4.5 (m, 2H); 6.8 (d, 1H); 7.4 (dd, 1H); 8.0 (d, 1H).

Example for the preparation of compounds XVI by process 14)

5-(2-Ethoxyethoxy)-2-methylpyridine

A solution of 994 g (18.4 mmol) of sodium methylate in 20 ml of abs. methanol is added dropwise to a solution of 2 g (18.4 mmol) of 5-hydroxy-2-methylpyridine in 20 ml of abs. methanol. The mixture is stirred for 5 minutes and then a solution of 5.83 g (23.9 mmol) of (2-ethoxy)ethyl p-toluenesulphonate in 15 ml of abs. methanol is added. The mixture is heated under reflux for 72 hours. It is evaporated to dryness, the residue is taken up in ethyl acetate and washed with saturated NaCl solution. Drying over sodium sulphate and evaporation result in 2.1 g (70% of theory) of a pale yellow oil.

$^1$H NMR (CDCl$_3$, δ [ppm]): 1.2 (t, 3H); 2.5 (s, 3H); 3.6 (q, 2H); 3.8 (m, 2H); 4.15 (m, 2H); 7.05 (d, 1H); 7.15 (dd, 1H); 8.2 (d, 1H).

Example for the preparation of compounds XV by process 16)

1-[2-(2-Ethoxyethoxy)-5-pyridyl]-2-nitro-1-propene

A mixture of 8.3 g (42.6 mmol) of 2-(2-ethoxyethoxy)-pyridine-5-alkehyde, 5.53 g, (73.7 mmol) of nitroethane and 3.83 g (49.7 mmol) of ammonium acetate in 50 ml of glacial acetic acid is heated under reflux for 7 hours. The mixture is then diluted with water while cooling in ice, and the product is filtered off with suction.

Yield: 4.8 g (45% of theory), melting point 75° C.

Example for the preparation of compounds XVIII by process 18a)

2-(2-Ethoxyethoxy)-pyridine-5-aldehyde

A total of 16 g of manganese dioxide is added in portions to a boiling solution of 8 g (40.6 mmol) of [2-(2-ethoxyethoxy)-5-pyridyl]-methanol in 200 ml of toluene within two hours. The mixture is then filtered hot and evaporated. Pale yellow oil, yield 7.1 g (90% of theory).

$^1$H NMR (CDCl$_3$; δ [ppm]): 1.2 (t, 3H); 3.6 (q, 2H); 3.8 (t, 2H); 4.6 (t, 2H); 6.9 (d, 1H); 8.1 (dd, 1H); 8.6 (d, 1H); 10.0 (s, 1H).

Examole for the preoaration of comoounds of the formula XVIII bv process 18 b

2-(2-Ethoxy-ethyleneoxy)-5-formyl-pyridine 1.3 g (32.5 mmol) of powdered NaOH are dissolved in 10 ml (0.1 mol) of 2-ethoxyethanol and then, at a temperature of 70° C., 2 g (10 mmol) of 3-trichloromethylpyridine are added dropwise within 30 minutes.

The mixture is then stirred at 80° C. for 2 hours, subsequently cooled to room temperature and filtered with suction. The filtrate is evaporated, and 20 ml of water are added to the residue. The mixture is adjusted to pH 3 with 2N hydrochloric acid and then stirred at room temperature for 2 hours. Thereafter 100 ml of CH$_2$Cl$_2$ are added and thoroughly stirred. The organic phase is 15 separated off, washed with water, dried with Na$_2$SO$_4$ and evaporated. The residue is distilled in a kugelrohr connected to an oil pump.

Yield: 970 mg of yellow oil, content: 85% (GC/MS)
$^1$H-NMR (CDCl$_3$; δ [ppm]: 9,6 (d, 1H, J=2,3 HH$_{a-rom}$),
8,1 (dd, 1H, J$_1$=2,3 Hz);
6,9 (d, 1H, J$_1$=8,7 Hz);
4,6 (t, 2H, —O—CH$_2$—);
3,85 (t, 2H, —O—CH$_2$—);
3,6 (q, 2H, —O—Et);
1,25 (t, 3H, —O—Et)

Example for the preparation of compounds XIX by process 20)

[2-(2-Ethoxyethoxy)-5-pyridyl]-methanol 40 ml of a 1M solution of borane in tetrahydrofuran are added dropwise at 0° C. to a solution of 2.11 g (10 mmol) of 6-(2-ethoxyethoxy)-nicotinic acid in 40 ml of abs. tetrahydrofuran. The mixture is stirred at room temperature for 3 hours and then acidified with concentrated hydrochloric acid, while cooling, then stirred for 30 minutes and evaporated to dryness. The residue is partitioned between ethyl acetate and saturated sodium carbonate solution, and the aqueous phase is extracted once more with ethyl acetate. The combined organic phases are washed with saturated NaCl solution, dried over sodium sulphate and evaporated. The residue crystallizes on trituration with pentane.

Colorless crystals, yield: 1.6 g (81% of theory), melting point: 48° C.

Example for the oreoaration of comoounds XX bv process 22)

6-(2-Ethoxyethoxy)-nicotinic acid

A suspension of 13.2 g (84 mmol) of 6-chloronicotinic acid, 21.2 g (0.53 mol) of powdered sodium hydroxide, 9.5 g (0.106 mol) of 2-ethoxyethanol and 2.64 g (8.2 mmol) of tetrabutylammonium bromide in 350 ml of abs. toluene is heated under reflux for 15 hours. The mixture is evaporated to dryness, and 10% strength hydrochloric acid is added to the residue, while cooling, until the mixture has pH 4. The precipitated acid is filtered off with suction.

Yield: 13.6 g (77% of theory); melting point: 125° C.

Examole for the preparation of compounds XXII bv process 24

2-(2-Ethoxy-ethyleneoxy)-5-(2-formylamino-2-methylpropyl)-pyridine 933 mg (18 mmol) of NaCN are cautiously introduced at a temperature of 0° C. into 5.5 ml of 96% strength sulphuric acid. 2 g (7.9 mmol) of 2-(2-ethoxyethyleneoxy)-5-(2,2-dimethyl-vinyl)pyridine are added dropwise at 0° C. After the addition is complete, the mixture is warmed to 20° C. on a water bath and stirred for 15 minutes. For working up, it is cautiously added dropwise to NaHCO$_3$ solution and extracted twice with 100 ml of dichloromethane each time. It is dried over Na$_2$SO$_4$ and evaporated. The residue is purified by chromatography on silica gel.

Mobile phase: ethyl acetate
Yield: 1.71 g of yellow oil (81% of theory)
$^1$H NMR (DMSO-D$_6$) δ [ppm]: 7.5 (d, 1H, formyl);
7.88 (d, 1H, H$_{arom}$);
7.48 (dd, 1H, H$_{arom}$);
6.75 (d, 1H, H$_{arom}$);
4.32 (t, 2H, —O—CH$_2$—);
3.17 (t, 2H, —O—CH$_2$—);
3.49 (q, 2H, —O—ET);
2.92 (s, 2H, Ar—CH$_2$—);
1.2 (s, 6H, —CH$_3$);
1.12 (t, 3H, —O—Et)

2-(2-Ethoxy-ethyleneoxy)-5-(2-acetamino-2-methylpropyl)pyridine

A mixture of 1 g (4.52 mmol), 2-(2-ethoxy-ethleneoxy)-5-(2,2-dimethylvinyl)-pyridine and 0.48 ml (9.2 mol) of acetonitrile is slowly added dropwise at room temperature, with stirring, to 2.5 ml of 96% strength sulphuric acid. The mixture is subsequently stirred for 30 minutes and then cautiously added dropwise to NaHCO$_3$ solution. It is extracted with CH$_2$Cl$_2$, the extract is dried with Na$_2$SO$_4$ and evaporated.

Residue: 0.9 g
Content: 95% (GC/MS)
Melting point: 87° C.

Example for the preparation of compounds XXIII by process 26 a

2-(2-Ethoxy-ethyleneoxy)-5-(2,2-dimethylvinyl)-pyridine 20 g (content 92%, 7.7 mmol) of 2-(2-ethoxyethyleneoxy-5-(1-hydroxy-2-methyl-propyl)-pyridine, 2 g (10.6 mmol) of p-toluenesulphonic acid hydrate and 200 ml of toluene are heated under reflux for 6 hours. After cooling, the mixture is washed with saturated NaHCO$_3$ solution, dried with Na$_2$SO$_4$ and evaporated. The residue is purified by column chromatography on silica gel with CH$_2$Cl$_2$/ethyl acetate as mobile phase.

Yield: 3.84 g (22% of theory) of yellow oil
$^1$H NMR (CDCl$_3$) δ [ppm]: 8.0 (d, 1H, H$_{arom}$);
7.45 (dd, 1H, H$_{arom}$);
6.75 (d, 1H, H$_{arom}$);
6.1 (s, 1H, H$_{vinyl}$);
4.5 (t, 2H, —O—CH$_2$—);
3.8 (t, 2H, —O—CH$_2$—);
3.6 (q, 2H, —O—Et);
1.9 (s, 3H, CH$_3$);
1.25 (t, 3H, —O—Et)

Examoles for the preoaration of compounds XXIII by process 26 b 2-(2-Ethoxy-ethyleneoxy)-5-(1-chloro-2-methyl-propyl)pyridine 23 g (content 86%, 78 mmol) of 2-(2-ethoxyethyleneoxy-5-(1-hydroxy-2-methyl-propyl)-pyridine are added to 220 ml of dry CHCl$_3$ and subsequently, while cooling in ice, 10.1 ml (0.14 mol) of thionyl chloride are added dropwise. After the addition is complete, the mixture is stirred at room temperature for one more hour and then added dropwise to NaHCO$_3$ solution with stirring. The organic phase is separated off, and the aqueous phase is extracted with CHCl$_3$. The combined organic phases are dried with Na$_2$SO$_4$ and evaporated.

Yield: 23.8 g
Content: 86%, (GC/MS) yellow oil
$^1$H NMR (CDCl$_3$) δ [ppm]: 8.03 (d, 1H, H$_{arom}$);
7.6 (dd, 1H, H$_{arom}$),
6.8 (d, 1H, H$_{arom}$);
4.6 (d, 1H, —CH—Cl);
4.5 (t, 2H, —O—CH$_2$—);
3.8 (t, 2H, —O—CH$_2$—);
3.6 (q, 2H, —O—Et);
2.2 (m, 1H, i-propyl);
1.25 (t, 3H, —OEt);
1.1 (d, 3H, i-propyl);
0.88 (d, 3H, i-propyl);

28 g (content 87%, 95 mmol) of 2-(2-ethoxyethyleneoxy-5-(1-chloro-2-methyl-propyl)-pyridine are added to 140 ml of diazabicycloundecene and heated under reflux for one hour. After cooling, the mixture is added to NaHCO$_3$ solution and extracted with ether. The extract is washed twice with NaHCO$_3$ solution, dried with Na$_2$SO$_4$ and evaporated.

Residue: 21.2 g of yellow oil
Content: 87% (GC/MS)

Examole for the preoaration of compounds XXIV by provess 28

2-(Ethoxy-ethyleneoxy)-5-(1-hydroxy-2methyl-propyl)pyridine

Dry ether is poured over 6.5 g (0.271 g) of magnesium turnings and the reaction is started by a few drops of 2-bromopropane.

Then 25.2 ml (0.271 mol) of 2-bromopropane dissolved in 280 ml of dry ether are added dropwise within 60 minutes, and the mixture is then stirred for 30 minutes. Subsequently 27 g (content 85%, 0.118 mmol) of 2-(2-ethoxyethyleneoxy)-pyridine-5-carbaldehyde dissolved in 130 ml of dry ether are added dropwise and heated under reflux for one hour. For working up, the mixture is cooled, poured into 2 l of saturated NH$_4$Cl solution, the organic phase is separated off, the aqueous phase is extracted with ether, and drying with Na$_2$SO$_4$ is followed by evaporation.

Residue: 30 g of yellow oil, content: 92% (GC/MS)
$^1$H NMR (CDCl$_3$) δ [ppm]: 8.0 (d, 1H, H$_{arom}$);
7.55 (dd, 1H, H$_{arom}$);
6.8 (d, 1H, H$_{arom}$);
4.45 (t, 2H, —O—CH$_2$);
4.3 (d, 1H, —CH—OH);
3.25 (t, 2H, —O—CH$_2$—);
3.1 (q, 2H, —O—Et);
1.9 (m, 1H, i-propyl);
1.25 (t, 3H, —OEt);
1.0 (d, 3H, i-propyl);
0.75 (d, 3H, i-propyl);

It is understood that the specification and examples are illustrative but not limitative of the present invention and that other embodiments within tl:e spirit and scope of the invention will suggest themselves to those skilled in the art.

What is claimed is:

1. Heteroarylethanol-pyridylalkylamine of the formula

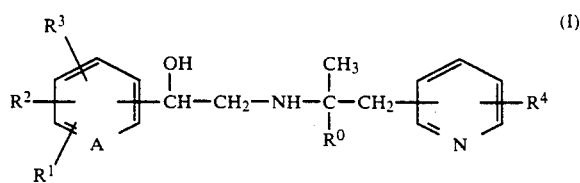

in which
R$^0$ represents hydrogen or methyl,
R$^1$ and R$^3$ each independently represents hydrogen, hydroxyl, halogen, alky, halogenoalkyl and hydroxyalkyl,
R$^2$ represents hydrogen, hydroxyl, alkoxy or the radical —NF$^5$R$^6$,
R$^4$ represents hydrogen, C$_1$-C$_{10}$-alkyl which is optionally substituted by hydroxyl, alkoxy or the radical —O—Z—R$^{10}$.
Z represents C$_1$-C$_{10}$-alkylene, -alkenylene or alkynylene,
R$^5$ represents hydrogen or alkyl,
R$^6$ represents hydrogen or alkyl,
R$^{10}$ represents hydroxyl, alkoxy, acyloxy, optionally substituted aryloxy or aralkyloxy,
with the substituent R$^4$ and the alkylamino group in the pyridyl ring of the formula I being in the p position with respect to one another, or a physiologically tolerated salt thereof, or optionally the N-oxide thereof.

2. A compound, salt or N-oxide according to claim 1 in which
R$^1$ and R$^3$ each independently represents hydrogen, hydroxyl, fluorine, chloring, bromine, C$_1$-C$_4$-alkyl, C$_1$-C$_4$-halogenoalkyl or hydroxymethyl,
R$^4$ represents hydrogen, C$_1$-C$_6$-alkyl which is optionally substituted by hydroxyl, C$_1$-C$_6$-alkoxy or the radical —O—Z—R$^{10}$,
Z represents C$_1$-C$_6$alkylene, C$_2$-C$_6$-alkenylene or C$_2$-C$_6$-alkynylene,
R$^5$ represents hydrogen or C$_1$-C$_6$-alkyl,
R$^6$ represents hydrogen or C$_1$-C$_6$-alkyl, and $R^{10}$ represents hydroxyl, $C_1$-$C_6$-alkoxy, $C_1$-$C_6$-acyloxy, optionally substituted aryloxy or aralkyloxy.

3. A compound, salt or N-oxide according to claim 1, in which
$R^1$ and $R^3$ each independently represent hydrogen, methyl, ethyl, fluorine, chlorine, bromine, hydroxyl, hydroxymethyl or $C_1$-$C_4$-alkoxy,
$R^2$ represents hydrogen, hydroxyl, $C_1$-$C_4$-alkoxy or the radical —$NR^5R^6$,
$R^4$ represents hydrogen, $C_1$-$C_3$-alkyl which is unsubstituted or substituted by hydroxyl, $C_1$-$C_3$-alkoxy or the radical —O—Z—$R^{10}$,
Z represents $C_1$-$C_4$-alkylene, $C_2$-$C_4$-alkenylene or $C_2$-$C_4$-alkynylene,
$R^5$ represents hydrogen or $C_1$-$C_c$-alkyl,
$R^6$ represents hydrogen or methyl, and
$R^{10}$ represents hydroxyl, $C_1$-$C_3$-alkoxy, $C_1$-$C_3$-acyloxy, or optionally substituted aryloxy or aralkyloxy.

4. A compound, salt or N-oxide according to claim 3, in which
$R^4$ represents —O—Z—$R^{10}$.

5. A composition for promoting production of livestock or controlling obesity in humans and animals, comprising an amount effective therefor of a compound or salt thereof according to claim 1 and a diluent.

6. A method of promoting production of livestock or for controlling obesity in humans and animals which comprises administering to such livestock, humans or animals an amount effective therefor of a compound or salt thereof according to claim 1.

* * * * *

UNITED STATES PATENT AND TRADEMARK OFFICE
CERTIFICATE OF CORRECTION

PATENT NO. : 5,028,617
DATED : July 2, 1991
INVENTOR(S) : Lindel et al.

It is certified that error appears in the above-identified patent and that said Letters Patent is hereby corrected as shown below:

Col. 66, claim 1, line 39, delete "alky" and substitute --alkyl--.

Signed and Sealed this

Twenty-first Day of September, 1993

Attest:

BRUCE LEHMAN

Attesting Officer                Commissioner of Patents and Trademarks

UNITED STATES PATENT AND TRADEMARK OFFICE
CERTIFICATE OF CORRECTION

PATENT NO. : 5,028,617

DATED : July 2, 1991

INVENTOR(S) : Lindel et al.

It is certified that error appears in the above-identified patent and that said Letters Patent is hereby corrected as shown below:

Col. 66, line 30    Delete " 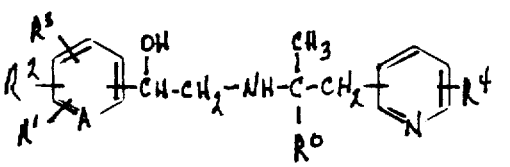 " and substitute -- 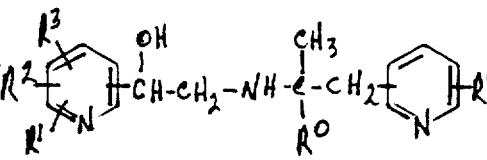 --

Col. 66, line 39 Delete "alky" and insert --alkyl--.

Col. 66, line 42    Delete " $-NF^5R^6$ " and substitute -- $-NR^5R^6$ --

Col. 67, last line  Delete " $C_1-C_C-$ " and substitute -- $C_1-C_3-$ --

Signed and Sealed this

Fifteenth Day of February, 1994

Attest:

BRUCE LEHMAN

Attesting Officer

Commissioner of Patents and Trademarks